United States Patent
Babakhani et al.

(10) Patent No.: US 11,515,733 B2
(45) Date of Patent: Nov. 29, 2022

(54) INTEGRATED ENERGY HARVESTING TRANSCEIVERS AND TRANSMITTERS WITH DUAL-ANTENNA ARCHITECTURE FOR MINIATURIZED IMPLANTS AND ELECTROCHEMICAL SENSORS

(71) Applicant: The Regents of the University of California, Oakland, CA (US)

(72) Inventors: Aydin Babakhani, Los Angeles, CA (US); Hamed Rahmani, Belle Mead, NJ (US); Hidemasa Mitsui, Santa Clara, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 17/456,328

(22) Filed: Nov. 23, 2021

(65) Prior Publication Data

US 2022/0158497 A1    May 19, 2022

Related U.S. Application Data

(63) Continuation of application No. PCT/US2021/020343, filed on Mar. 1, 2021.
(Continued)

(51) Int. Cl.
*H02J 50/27* (2016.01)
*H02J 50/00* (2016.01)

(52) U.S. Cl.
CPC ............ *H02J 50/27* (2016.02); *H02J 50/001* (2020.01)

(58) Field of Classification Search
CPC ........ H02J 50/001; H02J 50/005; H02J 50/20; H02J 50/12; H02J 50/27; H04B 5/00; H04B 7/00
See application file for complete search history.

(56) References Cited

U.S. PATENT DOCUMENTS 4,388,927 A    6/1983    Schober
4,612,940 A    9/1986    Kasevich et al.
(Continued)

FOREIGN PATENT DOCUMENTS

AU    2018217270 A1    8/2018
CN    104767291 A    7/2015
(Continued)

OTHER PUBLICATIONS

Razavi, "Design of analog CMOS Integrated Circuits", McGraw-Hill Series in Electrical and Computer Engineering, 2001, 706 pgs., (presented in eight parts).
(Continued)

*Primary Examiner* — Rexford N Barnie
*Assistant Examiner* — Joseph N Inge
(74) *Attorney, Agent, or Firm* — KPPB LLP

(57) ABSTRACT

Systems and methods for utilizing a small form-factor, wirelessly powered transceiver are disclosed. In one embodiment, a wireless powered transceiver includes a receive antenna configured to receive a receive signal, a transmit antenna configured to transmit a transmit signal, a power harvesting system including a rectifier circuit configured convert radio frequency energy from the receive signal into DC (direct current) voltage, and a power management unit (PMU) configured to set the operating mode and biasing condition of the receive and transmit circuitry blocks and provide DC voltage from the receive circuitry block to the transmit circuitry block to maintain a minimum voltage, a receiver circuitry block configured to provide energy from the receive signal to the power harvesting system, and a transmitter circuitry block including a data modulator circuit, the data modulator circuit configured to generate the transmit signal using DC voltage received from the power management unit.

23 Claims, 28 Drawing Sheets

Related U.S. Application Data

(60) Provisional application No. 63/136,096, filed on Jan. 11, 2021, provisional application No. 62/983,494, filed on Feb. 28, 2020.

(56) References Cited

U.S. PATENT DOCUMENTS

| | | | |
|---|---|---|---|
| 4,719,919 | A | 1/1988 | Marchosky et al. |
| 5,464,429 | A | 11/1995 | Hedberg et al. |
| 5,522,865 | A | 6/1996 | Schulman et al. |
| 5,749,909 | A | 5/1998 | Schroeppel et al. |
| 7,043,301 | B1 | 5/2006 | Kroll et al. |
| 7,610,092 | B2 | 10/2009 | Cowan et al. |
| 8,634,919 | B1 | 1/2014 | Hou et al. |
| 8,644,933 | B2 | 2/2014 | Ozawa et al. |
| 9,031,658 | B2 | 5/2015 | Chiao et al. |
| 9,037,223 | B2 | 5/2015 | Oral et al. |
| 9,168,380 | B1 | 10/2015 | Greenhut et al. |
| 9,270,137 | B2 | 2/2016 | Greene |
| 9,711,978 | B2 | 7/2017 | Manova-elssibony et al. |
| 10,493,288 | B2 | 12/2019 | Hastings et al. |
| 2002/0064245 | A1 | 5/2002 | McCorkle |
| 2002/0103507 | A1 | 8/2002 | Helland |
| 2002/0137991 | A1 | 9/2002 | Scarantino et al. |
| 2003/0032986 | A1 | 2/2003 | Kupper |
| 2004/0054471 | A1 | 3/2004 | Bartlett et al. |
| 2004/0058186 | A1 | 3/2004 | Daulton |
| 2004/0095287 | A1 | 5/2004 | Mohamadi |
| 2004/0108954 | A1 | 6/2004 | Richley et al. |
| 2005/0058121 | A1 | 3/2005 | Santhoff et al. |
| 2005/0256549 | A1 | 11/2005 | Holzer |
| 2006/0136004 | A1 | 6/2006 | Cowan et al. |
| 2007/0118187 | A1 | 5/2007 | Denker et al. |
| 2007/0120677 | A1 | 5/2007 | Park et al. |
| 2007/0293895 | A1 | 12/2007 | Cowan et al. |
| 2008/0021505 | A1 | 1/2008 | Hastings et al. |
| 2008/0252422 | A1 | 10/2008 | Dowla et al. |
| 2008/0262580 | A1 | 10/2008 | Gerber et al. |
| 2008/0300660 | A1 | 12/2008 | John |
| 2009/0157141 | A1 | 6/2009 | Chiao et al. |
| 2009/0219139 | A1* | 9/2009 | Slesinski ............ G06K 19/0707 340/10.1 |
| 2010/0076517 | A1 | 3/2010 | Imran |
| 2010/0114189 | A1 | 5/2010 | Donofrio et al. |
| 2010/0114243 | A1* | 5/2010 | Nowak ................ H04B 1/14 607/60 |
| 2011/0022025 | A1 | 1/2011 | Savoie et al. |
| 2011/0288615 | A1 | 11/2011 | Armstrong et al. |
| 2012/0008714 | A1* | 1/2012 | Rizwan ................ A61B 5/0028 375/295 |
| 2012/0239118 | A1 | 9/2012 | Ozawa et al. |
| 2012/0256492 | A1 | 10/2012 | Song et al. |
| 2013/0066400 | A1 | 3/2013 | Perryman et al. |
| 2013/0123882 | A1 | 5/2013 | Towe |
| 2014/0046389 | A1 | 2/2014 | Anderson et al. |
| 2014/0058239 | A1 | 2/2014 | Joshi et al. |
| 2014/0198062 | A1 | 7/2014 | Kreutzer et al. |
| 2014/0243848 | A1 | 8/2014 | Auricchio et al. |
| 2014/0252543 | A1 | 9/2014 | Li et al. |
| 2014/0336474 | A1* | 11/2014 | Arbabian ................ H02J 50/90 600/300 |
| 2014/0375261 | A1* | 12/2014 | Manova-Elssibony ...................... H02J 50/23 320/108 |
| 2015/0042358 | A1 | 2/2015 | Lin et al. |
| 2015/0076920 | A1* | 3/2015 | Zargham ................ H02J 50/12 307/104 |
| 2015/0127068 | A1 | 5/2015 | Simon et al. |
| 2015/0157868 | A1 | 6/2015 | Franke et al. |
| 2015/0217123 | A1 | 8/2015 | Deterre et al. |
| 2015/0229139 | A1 | 8/2015 | Greene |
| 2015/0297900 | A1 | 10/2015 | Perryman et al. |
| 2015/0343205 | A1 | 12/2015 | Howard et al. |
| 2015/0356332 | A1 | 12/2015 | Turner et al. |
| 2016/0008602 | A1 | 1/2016 | Perryman et al. |
| 2016/0038739 | A1 | 2/2016 | Liu et al. |
| 2016/0048710 | A1 | 2/2016 | Nekoogar et al. |
| 2016/0149441 | A1 | 5/2016 | Nayak |
| 2016/0338798 | A1 | 11/2016 | Vora et al. |
| 2017/0001003 | A1 | 1/2017 | Pivonka et al. |
| 2018/0069486 | A1 | 3/2018 | Ouda et al. |
| 2018/0123639 | A1 | 5/2018 | Muthali et al. |
| 2018/0235692 | A1 | 8/2018 | Efimov et al. |
| 2019/0097430 | A1* | 3/2019 | Bae ......................... H02J 50/20 |
| 2019/0143097 | A1 | 5/2019 | John et al. |
| 2019/0180065 | A1 | 6/2019 | Babakhani et al. |
| 2019/0224476 | A1 | 7/2019 | Sun et al. |
| 2019/0247664 | A1 | 8/2019 | Irazoqui et al. |
| 2019/0262605 | A1* | 8/2019 | Babakhani .......... A61N 1/37205 |
| 2019/0326785 | A1 | 10/2019 | Freitas et al. |
| 2019/0374777 | A1 | 12/2019 | Burdick et al. |
| 2020/0022607 | A1 | 1/2020 | Pratt et al. |
| 2020/0155828 | A1 | 5/2020 | Shepard et al. |
| 2020/0195256 | A1* | 6/2020 | Emira ............... G06K 19/07773 |
| 2021/0023373 | A1 | 1/2021 | Deshazo et al. |
| 2021/0356417 | A1 | 11/2021 | Babakhani et al. |
| 2021/0397257 | A1* | 12/2021 | Rogers ..................... G06F 3/015 |
| 2022/0008736 | A1 | 1/2022 | Babakhani et al. |

FOREIGN PATENT DOCUMENTS

| | | |
|---|---|---|
| CN | 113228464 A | 8/2021 |
| EP | 3116385 B1 | 11/2019 |
| EP | 3884562 A1 | 9/2021 |
| EP | 4032165 A1 | 7/2022 |
| JP | 2019130360 A | 8/2019 |
| JP | 2022507813 A | 1/2022 |
| WO | 1996027327 A1 | 9/1996 |
| WO | 2000038783 A1 | 7/2000 |
| WO | 2007028035 A2 | 3/2007 |
| WO | 2007109656 A2 | 9/2007 |
| WO | 2013058958 A1 | 4/2013 |
| WO | 2016199142 A1 | 12/2016 |
| WO | 2017205565 A1 | 11/2017 |
| WO | 2018039162 A2 | 3/2018 |
| WO | 2018053467 A1 | 3/2018 |
| WO | 2020106440 A1 | 5/2020 |
| WO | 2020106862 A1 | 5/2020 |
| WO | 2020125839 A1 | 6/2020 |
| WO | 2020106440 A8 | 7/2020 |
| WO | 2020106440 A8 | 10/2020 |
| WO | 2021007071 A1 | 1/2021 |
| WO | 2021007210 A1 | 1/2021 |
| WO | 2021046313 A1 | 3/2021 |
| WO | 2021055146 A1 | 3/2021 |
| WO | 2021174215 A1 | 9/2021 |
| WO | 2021183487 A1 | 9/2021 |
| WO | 2021247490 A1 | 12/2021 |
| WO | 2022133501 A1 | 6/2022 |
| WO | 2022192894 A1 | 9/2022 |

OTHER PUBLICATIONS

Razavi, Behzad, "RF Microelectronics", New Jersey: Prentice Hall, 1998, vol. 1, 98 pgs. , Chapter 8: pp. 497-594.

Rodriguez et al., "Long-term results of electrical stimulation of the lower esophageal sphincter for the treatment of gastroesophageal reflux disease", Endoscopy, Aug. 2013, vol. 45, No. 8, pp. 595-604, DOI: 10.1055/s-0033-1344213.

Sample et al., "Analysis, Experimental Results, and Range Adaptation of Magnetically Coupled Resonators for Wireless Power Transfer", IEEE Transactions on Industrial Electronics, vol. 58, No. 2, Feb. 2011, pp. 544-554, DOI:10.1109/TIE.2010.2046002.

Sankaragomathi et al., "A 27w subcutaneous wireless biosensing platform with optical power and data transfer", Proceedings of the IEEE 2014 Custom Integrated Circuits Conference, Sep. 15, 2014, pp. 1-4.

Sayenko et al., "Spinal segment-specific transcutaneous stimulation differentially shapes activation pattern among motor pools in humans", Journal of Applied Physiology, 2015, vol. 118, pp. 1364-1374, first published Mar. 26, 2015; doi:10.1152/japplphysiol.01128.2014.

(56) References Cited

OTHER PUBLICATIONS

Shi et al., "A 10 mm3 Inductive Coupling Radio for Syringe-Implantable Smart Sensor Nodes", IEEE Journal of Solid-State Circuits, Nov. 2016, vol. 51, No. 11, pp. 2570-2583, DOI: 10.1109/JSSC.2016.2606162.
Shi et al., "A 10mm3 syringe-implantable near-field radio system on glass substrate", IEEE Int. Solid-State Circuits Conf. (ISSCC) Dig. Tech. Papers, pp. 448-449, Feb. 2016.
Silvetti et al., "Cardiac pacing in paediatric patients with congenital heart defects: transvenous or epicardial?", Europace, vol. 15, No. 9, Sep. 2013, published online Feb. 24, 2013, pp. 1280-1286, doi: 10.1093/europace/eut029.
Soontornpipit, "Design of an Implantable Antenna Feasibility Study for Continuous Glucose Monitoring", ECTI Transactions on Electrical Engineering, Electronics, and Communications, Feb. 2014, vol. 12, No. 1, pp. 44-52.
Stoopman et al., "Co-Design of a CMOS Rectifier and Small Loop Antenna for Highly Sensitive RF Energy Harvesters", IEEE Journal of Solid-State Circuits, Mar. 2014, vol. 49, Issue 3, pp. 622-634, DOI: 10.1109/JSSC.2014.2302793.
Sun et al., "A wirelessly powered injection-locked oscillator with on-chip antennas in 180nm SOI CMOS", 2016 IEEE MTT-S International Microwave Symposium (IMS), Aug. 11, 2016, pp. 1-3 [online], [retrieved on Aug. 14, 2020], Retrieved from the Internet <URL: https://ieeexplore.ieee.org/abstract/document/7540249>, entire document.
Sun et al., "A Wirelessly Powered Injection-Locked Oscillator With On-Chip Antennas in 180-nm SOI CMOS for Spectroscopy Application", IEEE Sensors Letters, vol. 3, No. 7, Jul. 3, 2019, pp. 1-4 [online], [retrieved on Aug. 14, 2020], Retrieved from the Internet <URL: https://ieeexplore.ieee.org/abstract/document/8754750>.
Tabesh et al., "A Power-Harvesting Pad-Less Millimeter-Sized Radio", IEEE Journal of Solid-State Circuits, Apr. 2015, vol. 50, Issue: 4, pp. 962-977, DOI: 10.1109/JSSC.2014.2384034.
Teh et al., "Design and analysis of UHF micropower CMOS DTMOST rectifiers", IEEE Transactions on Circuits and Systems—II: Express Briefs, Feb. 2009, vol. 56, No. 2, pp. 122-126, doi: 10.1109/TCSII.2008.2010190.
Theilmann et al., "A μW Complementary Bridge Rectifier With Near Zero Turn-on Voltage in SOS CMOS for Wireless Power Supplies", IEEE Transactions on Circuits and Systems I: Regular Papers, 2012, vol. 59, No. 9, pp. 2111-2124, DOI: 10.1109/TCSI.2012.2185293.
Tjong et al., "Permanent Leadless Cardiac Pacemaker Therapy a Comprehensive Review", Circulation, Apr. 11, 2017, vol. 135, pp. 1458-1470, DOI: 10.1161/CIRCULATIONAHA.116.025037.
Tolosa et al., "Electrochemically deposited iridium oxide reference electrode integrated with an electroenzymatic glutamate sensor on a multi-electrode array microprobe", Biosensors and Bioelectronics, 2013, vol. 42, pp. available online Nov. 6, 2012, pp. 256-260, http://dx.doi.org/10.1016/jbios.2012.10.061.
Van Dongen et al., "Does a coupling capacitor enhance the charge balance during neural stimulation? An empirical study", Medical & Biological Engineering and Computing, 2016, vol. 54, pp. 93-101, published online May 29, 2015, DOI 10.1007/S11517-015-1312-9.
Van Rees et al., "Implantation-related complications of implantable cardioverter-defibrillators and cardiac resynchronization therapy devices: a systematic review of randomized clinical trials", Journal of the American College of Cardiology, Aug. 30, 2011, vol. 58, Issue 10, pp. 995-1000, https://doi.org/10.1016/j.jacc.2011.06.007.
Wan et al., "Analysis and design of a thermoelectric energy harvesting system with reconfigurable array of thermoelectric generators for IoT applications", IEEE Transactions on Circuits and Systems I: Regular Papers, Sep. 2017, vol. 64, No. 9, pp. 2346-2358, DOI: 10.1109/TCSI.2017.2708763.
Weber et al., "A Miniaturized Single-Transducer Implantable Pressure Sensor With Time-Multiplexed Ultrasonic Data and Power Links", IEEE Journal of Solid-State Circuits, Apr. 2018, vol. 53, No. 4, pp. 1089-1101, DOI: 10.1109/JSSC.2017.2782086.
Weber et al., "Functional electrical stimulation using microstimulators to correct foot drop: a case study1", Canadian Journal of Physiology and Pharmacology, 2004, vol. 82, No. 8-9, first published Oct. 19, 2004, pp. 784-792, doi: 10.1139/Y04-078.
Xie et al., "Wireless power transfer and applications to sensor networks", IEEE Wireless Communications, Aug. 2013, vol. 20, Issue: 4, pp. 140-145, DOI: 10.1109/MWC.2013.6590061.
Xu et al., "A fully implantable stimulator with wireless power and data transmission for experimental investigation of epidural spinal cord stimulation", IEEE Transactions on Neural Systems and Rehabilitation Engineering, 2015, vol. 23, No. 4, pp. 683-692, DOI:10.1109/TNSRE.2015.2396574.
Yadav et al., "Low Voltage Low Power Sub-threshold Operational Amplifier in 180nm CMOS", 2017 IEEE Third International Conference on Sensing signal Processing and Security (ICSSS), 2017, 4 pgs.
Yi et al., "Analysis and design strategy of UHF micro-power CMOS rectifiers for micro-sensor and RFID applications", IEEE Transactions on Circuits and Systems I: Regular Papers, Jan. 15, 2007, vol. 54, Issue 1, pp. 153-166, DOI: 10.1109/TCSI.2006.887974.
Yu et al., "Cardiac resynchronization therapy: state of the art 2013", European Heart Journal, vol. 34, Issue 19, May 14, 2013, online published Jan. 25, 2013, pp. 1396-1403, https://doi.org/10.1093/eurheartj/ehs454.
Yvanoff et al., "A Feasibility Study of Tissue Characterization Using Implanted LC Sensors", IEEE Transactions on Antennas and Propagation, Apr. 2009, vol. 57, Issue 4, pp. 885-893DOI: 10.1109/TAP.2009.2016073.
Zargham et al., "Fully Integrated On-Chip Coil in 0.13 μm CMOS for Wireless Power Transfer Through Biological Media", IEEE Transactions on Biomedical Circuits and Systems, Apr. 2015, vol. 9, Issue 2, pp. 259-271, DOI: 10.1109/TBCAS.2014.2328318.
Zhang et al., "A 23 μA RF-powered transmitter for biomedical applications", 2011 IEEE Radio Frequency Integrated Circuits Symposium, 4 pgs., DOI: 10.1109/RFIC.2011.5940711.
Zhang et al., "A Miniature Mode Reconfigurable Inductorless IR-UWB Transmitter—Receiver for Wireless Short-Range Communication and Vital-Sign Sensing", IEEE Journal of Emerging and Selected Topics in Circuits and Systems, vol. 8, No. 2, Jun. 2018, pp. 294-305.
Balanis, Constantine A., "Antenna Theory: Analysis and Design", John Wiley & Sons, 2016, 1095 pgs. (presented in nine parts).
Bereuter et al., "Hot Topic in Cardiac Devices—Leadless cardiac dual-chamber pacing", Europace Abstracts Supplement, 2018, 1 pg. doi:10.1093/europace/euy015.
Bereuter et al., "Leadless Dual-Chamber Pacing, A Novel Communication Method for Wireless Pacemaker Synchronization", JACC: Basic to Translational Service, Dec. 2018, vol. 3, No. 6, pp. 813-823, https://doi.org/10.1016/j.jacbts.2018.07.009.
Biederman et al., "A Fully-Integrated, Miniaturized (0.125 mm$^2$) 10.5 μW Wireless Neural Sensor", IEEE Journal of Solid-State Circuits, vol. 48, No. 4, Mar. 22, 2013, pp. 960-970, DOI: 10.1109/JSSC.2013.2238994.
Bigio et al., "Microwave absorption spectroscopy of DNA", Biopolymers, Jan. 1993, vol. 33, Issue 1, pp. 147-150, https://doi.org/10.1002/bip.360330114.
Bourdel et al., "A 9-pJ/Pulse 1.42-Vpp OOK CMOS UWB Pulse Generator for the 3.1--10.6-GHz FCC Band", IEEE Transactions on Microwave Theory and Techniques, vol. 58, No. 1, Jan. 2010, pp. 1-9.
Brown et al., "An Ultra-Low-Power 9.8 GHz Crystal-Less UWB Transceiver With Digital Baseband Integrated in 0.18 μm BiCMOS", IEEE International Solid-State Circuits Conference, 2013, pp. 442-443.
Carlson et al., "A 20 mV Input Boost Converter With Efficient Digital Control for Thermoelectric Energy Harvesting", IEEE Journal of Solid-State Circuits, vol. 45, Issue 4, Apr. 2010, pp. 741-750.
Chae et al., "A 128-Channel 6 mW Wireless Neural Recording IC With Spike Feature Extraction and UWB Transmitter", IEEE Transactions on Neural Systems and Rehabilitation Engineering, vol. 17, No. 4, Aug. 2009, pp. 312-321.
Chang et al., "27.7 A 30.5mm3 fully packaged implantable device with duplex ultrasonic data and power links achieving 95kb/s with

(56) References Cited

OTHER PUBLICATIONS

<10-4 BER at 8.5cm depth", IEEE International Solid-State Circuits Conference (ISSCC), Feb. 5-9, 2017, pp. 460-461, DOI: 10.1109/ISSCC.2017.7870460.

Charthad et al., "A mm-sized implantable medical device (IMD) with ultrasonic power transfer and a hybrid bi-directional data link", IEEE Journal of Solid-State Circuits, vol. 50, Issue 8, Aug. 2015, pp. 1741-1753, DOI: 10.1109/JSSC.2015.2427336.

Charthad et al., "A mm-Sized Wireless Implantable Device for Electrical Stimulation of Peripheral Nerves", IEEE Transactions on Biomedical Circuits and Systems, vol. 12, No. 2, Apr. 2018, pp. 257-270, doi: 10.1109/TBCAS.2018.2799623.

Charthad et al., "System-Level Analysis of Far-Field Radio Frequency Power Delivery for mm-Sized Sensor Nodes", IEEE Transactions on Circuits and Systems I: Regular Papers, Feb. 3, 2016, vol. 63, No. 2, pp. 300-311, DOI: 10.1109/TCSI.2015.2512720.

Chen et al., "3D Radar Imaging based on a Synthetic Array of 30GHz Impulse Radiators with On-Chip Antennas in 130nm SiGe BiCMOS", IEEE Transactions on Microwave Theory and Techniques, Nov. 2017, vol. 65, No. 22, pp. 4373-4384.

Chen et al., "Multiple leadless pacemakers implanted in the right ventricle of swine", Europace, 2016, vol. 18, 1748-1752, published online Jan. 31, 2016, doi:10.1093/europace/euv418.

Cheng, "Field and wave electromagnetics", Pearson Education India, 1989, 720 pgs., (presented in three parts).

Chinitz et al., "Accelerometer-based atrioventricular synchronous pacing with a ventricular leadless pacemaker: Results from the Micra atrioventricular feasibility studies", Heart Rhythm, 2018, vol. 15, pp. 1363-1371, https://doi.org/10.1016/j.hrthm.2018.05.004.

Cogan, "Neural stimulation and recording electrodes", Annual Review of Biomedical Engineering, 2008, vol. 10, pp. 275-309, first published online Apr. 22, 2008, doi: 10.1146/annurev.bioeng.10.061807.160518.

Dagan et al., "A low-power low-cost 24 ghz rfid tag with a c-flash based embedded memory", IEEE Journal of Solid-State Circuits, Sep. 2014, vol. 49, No. 9, pp. 1942-1957, DOI: 10.1109/JSSC.2014.2323352.

Dagdeviren et al., "Conformal piezoelectric energy harvesting and storage from motions of the heart, lung, and diaphragm", PNAS, vol. 111, No. 5, Feb. 4, 2014, published online Jan. 21, 2014, pp. 1927-1932, doi: 10.1073/pnas.1317233111.

De Roover et al., "A fully integrated wireless power supply for pinless active RFID-devices in 130nm CMOS", 2007 IEEE Asian Solid-State Circuits Conference, Nov. 12-14, 2007, pp. 123-126, DOI: 10.1109/ASSCC.2007.4425747.

Deer et al., "The Appropriate Use of Neurostimulation: Avoidance and Treatment of Complications of Neurostimulation Therapies for the Treatment of Chronic Pain", Neuromodulation: Technology at the Neural Interface, Aug. 12, 2014, vol. 17, No. 6, pp. 571-598, DOI: 10.1111/ner.12206.

Derksen et al., "Tissue Discontinuities Affect Conduction Velocity Restitution", Circulation, Aug. 19, 2003, vol. 108, Issue 7, pp. 882-888, https://doi.org/10.1161/01.CIR.0000081766.16185.28.

Dickson, "On-chip high-voltage generation in MNOS integrated circuits using an improved voltage multiplier technique", IEEE Journal of Solid-State Circuits, 1976, vol. 11, No. 3, pp. 374-378, http://dx.doi.org/10.1109/JSSC.1976.1050739.

Dorta-Quinones et al., "A Wireless FSCV Monitoring IC With Analog Background Subtraction and UWB Telemetry", IEEE Transactions on Biomedical Circuits and Systems, vol. 10, No. 2, Apr. 2016, 36 pgs.

Dosdall et al., "Mechanisms of defibrillation", Annual Review of Biomedical Engineering, vol. 12, Aug. 15, 2010, first published as a Review in Advance May 5, 2010, pp. 233-258, https://doi.org/10.1146/annurev-bioeng-070909-105305.

Eldeeb et al., "A 0.4-V Miniature CMOS Current Mode Instrumentation Amplifier", IEEE Transactions on Circuits and Systems—II Express Briefs, Mar. 2018, Vo. 65, No. 3, pp. 261-265, DOI: 10.1109/TCSII.2017.2685589.

FCC, "First Report and Order 02-48", Federal Communication Commission (FCC), Feb. 2002, 118 pgs., (presented in two parts).

Fenton et al., "Termination of Atrial Fibrillation Using Pulsed Low-Energy Far-Field Stimulation", Circulation, Aug. 11, 2009, vol. 120, Issue 6, 467-476, first published Jul. 27, 2009, https://doi.org/10.1161/CIRCULATIONAHA.108.825091.

Gao et al., "A 71 GHz RF Energy Harvesting Tag with 8% Efficiency for Wireless Temperature Sensors in 65nm CMOS", IEEE Radio Frequency Integrated Circuits Symposium (RFIC), Jun. 2013, pp. 403-406, DOI: 10.1109/RFIC.2013.6569616.

Gilbert, "Impedance matching with lossy components", IEEE Transactions on Circuits and Systems, Feb. 1975, vol. 22, Issue: 2, pp. 96-100, DOI: 10.1109/TCS.1975.1084016.

Grenier et al., "Recent advances in microwave-based dielectric spectroscopy at the cellular level for cancer investigations", IEEE Transactions on Microwave Theory and Techniques, Apr. 11, 2013, vol. 61, No. 5, pp. 2023-2030, doi: 10.1109/TMTT.2013.2255885.

Guler et al., "Power Management in Wireless Power-Sipping Devices: A Survey", IEEE Circuits and Systems Magazine, Nov. 20, 2017, pp. 64-82, DOI: 10.1109/MCAS .2017.2757090.

Gunturi et al., "A 250-Mb/s Data Rate IR-UWB Transmitter Using Current-Reused Technique", IEEE Transactions on Microwave Theory and Techniques, vol. 65, No. 11, Nov. 2017, pp. 4255-4265, DOI:10.1109/TMTT.2017.2695189.

Hannan et al., "Energy harvesting for the implantable biomedical devices: issues and challenges", BioMedical Engineering OnLine, 2014, vol. 13, No. 79, 23 pgs., https://doi.org/10.1186/1475-925X-13-79.

Hehn et al., "A Fully Autonomous Integrated Interface Circuit for Piezoelectric Harvesters", IEEE Journal of Solid-State Circuits, Sep. 2012, vol. 47, Issue 9, pp. 2185-2198, DOI: 10.1109/JSSC.2012.2200530.

Higgins et al., "Advances in Pacing Therapy: Examining the Potential Impact of Leadless Pacing Therapy", Journal of Innovations in Cardiac Rhythm Management, Nov. 2014, vol. 5, pp. 1825-1833, DOI: 10.19102/icrm.2014.051106.

Ho et al., "Wireless power transfer to deep-tissue microimplants", PNAS, vol. 111, No. 22, Jun. 3, 2014, first published May 19, 2014, pp. 7974-7979, https://doi.org/10.1073/pnas.1403002111.

Huang et al., "A simple subthreshold cmos voltage reference circuit with channel-length modulation compensation", IEEE Transactions on Circuits and Systems—II: Express Briefs, Sep. 2006, vol. 53, No. 9, pp. 882-885, DOI: 10.1109/TCSII.2006.881813.

Huang et al., "Materials and designs for wireless epidermal sensors of hydration and strain", Advanced Functional Materials, Jul. 2, 2014, vol. 24, Issue 25, pp. 3846-3854, first published Mar. 2, 2014, doi: 10.1002/adfm.201303886.

Huang et al., "Neurostimulation Strategy for Stress Urinary Incontinence", IEEE Transactions on Neural Systems and Rehabilitation Engineering, Jul. 2017, vol. 25, No. 7, pp. 1068-1078, first published Mar. 7, 2017, doi: 10.1109/TNSRE.2017.2679077.

Jawad et al., "Opportunities and Challenges for Near-Field Wireless Power Transfer: A Review", Energies, vol. 10, No. 1022, Jul. 18, 2017, 28 pgs., doi:10.3390/en10071022.

Jeon et al., "A 143nW Glucose-Monitoring Smart Contact Lens IC with a Dual-Mode Transmitter for Wireless-Powered Backscattering and RF-Radiated Transmission Using a Single Loop Antenna", Symposium on VLSI Circuits, Jun. 9-14, 2019, pp. C294-C295, DOI: 10.23919/VLSIC.2019.8777984.

Jia et al., "A mm-sized free-floating wirelessly powered implantable optical stimulating system-on-a-chip", 2018 IEEE International Solid—State Circuits Conference—(ISSCC), Feb. 11-15, 2018, San Francisco, CA, pp. 468-470, DOI: 10.1109/ISSCC.2018.8310387.

Jiang et al., "A Sub-1 µW Multiparameter Injectable BioMote for Continuous Alcohol Monitoring", IEEE Custom Integrated Circuits Conference (CICC), 2018, pp. 1-4.

Johnson et al., "StimDust: A 6.5 mm3, wireless ultrasonic peripheral nerve stimulator with 82% peak chip efficiency", UC Berkeley, Retrieved from https://escholarship.org/uc/item/8px811qc, published May 5, 2019, 5 pgs., http://dx.doi.org/10.1109/CICC.2018.8357047.

Kang et al., "A 1.7×4.1×2 mm3 Fully Integrated pH Sensor for Implantable Applications Using Differential Sensing and Drift-

(56) References Cited

OTHER PUBLICATIONS

Compensation", 2019 Symposium on VLSI Circuits Digest of Technical Papers, C25-1, pp. C310-C311.
Kang et al., "Design and Optimization of Area-Constrained Wirelessly Powered CMOS UWB SoC for localization applications", IEEE Transactions on Microwave Theory and Techniques, Apr. 2016, vol. 64, No. 4, pp. 1042-1054, DOI: 10.1109/TMTT.2016. 2536663.
Karthaus et al., "Fully Integrated Passive UHF RFID Transponder IC With 16.7-µW Minimum RF Input Power", IEEE Journal of Solid State Circuits, Oct. 2003, vol. 38, No. 10, pp. 1602-1608, DOI: 10.1109/JSSC.2003.817249.
Kelly et al., "A power-efficient neural tissue stimulator with energy Yecovery", IEEE Transactions on Biomedical Circuits and Systems, Feb. 2011, vol. 5, Issue 1, pp. 20-29, first published Jan. 24, 2011, DOI: 10.1109/TBCAS.2010.2076384.
Kennedy et al., "High intensity focused ultrasound: surgery of the future?", British Journal of Radiology, Sep. 2003, vol. 76, No. 909, pp. 590-599, doi: 10.1259/bjr/17150274.
Kim et al., "A 144-MHz Fully Integrated Resonant Regulating Rectifier With Hybrid Pulse Modulation for mm-Sized Implants", IEEE Journal of Solid-State Circuits, Nov. 2017, vol. 52, Issue 11, pp. 3043-3055, DOI: 10.1109/JSSC.2017.2734901.
Kim et al., "Design of miniaturized wireless power receivers for mm-sized implants", 2017 IEEE Custom Integrated Circuits Conference (CICC), Apr. 30-May 30, 2017, 8 pgs., DOI: 10.1109/CICC. 2017.7993703.
Kim et al., "Wireless power transfer to a cardiac implant", Applied Physics Letters, vol. 101, 2012, pp. 073701-1-073701-4; doi: 10.1063/ 1.4745600.
Kocer et al., "A new transponder architecture with on-chip ADC for long-range telemetry applications", IEEE Journal of Solid-State Circuits, vol. 41, No. 5, Apr. 24, 2006, pp. 1142-1148 [online], [retrieved on Aug. 14, 2020], Retrieved from the Internet <URL: https://www.mpflynngroup.com/uploads/7/3/4/9/73490609/01624404. pdf>, entire document, especially: fig. 1, p. 1, col. 2, para. 3; p. 2, col. 2, para 2.
Kotani et al., "High-Efficiency Differential-Drive CMOS Rectifier for UHF RFIDs", IEEE Journal of Solid-State Circuits, Nov. 2009, vol. 44, Issue 11, pp. 3011-3018, DOI:10.1109/JSSC.2009. 2028955.
Kulkarni et al., "A 750 Mb/s, 12 pJ/b, 6-to-10 GHz CMOS IR-UWB Transmitter with Embedded On-Chip Antenna", IEEE Journal of Solid-State Circuits, vol. 44, No. 2, Feb. 2009, pp. 394-403, DOI: 10.1109/JSSC.2008.2011034.
Kuo et al., "Near-field power transfer and backscattering communication to miniature RFID tag in 65 nm CMOS technology", 2016 IEEE MTT-S International Microwave Symposium (IMS), May 22-27, 2016, 4 pgs., DOI: 10.1109/MWSYM.2016.7540221.
Kurs et al., "Wireless Power Transfer via Strongly Coupled Magnetic Resonances", Science, vol. 317, No. 5834, Jul. 6, 2007, published online Jun. 7, 2007, pp. 83-86, DOI: 10.1126/science. 1143254.
Le et al., "Efficient Far-Field Radio Frequency Energy Harvesting for Passively Powered Sensor Networks", IEEE Journal of Solid-State Circuits, May 2008, vol. 43, No. 5, pp. 1287-1302, DOI: 10.1109/JSSC.2008.920318.
Lepock, "Cellular effects of hyperthermia: relevance to the minimum dose for thermal damage", International Journal of Hyperthermia, vol. 19, No. 3, May-Jun. 2003, pp. 252-266, DOI: 10.1080/ 0265673031000065042.
Li et al., "A 13.56 MHz Wireless Power Transfer System With Reconfigurable Resonant Regulating Rectifier and Wireless Power Control for Implantable Medical Devices", IEEE Journal of Solid-State Circuits, vol. 50, No. 4, Apr. 1, 2015, pp. 978-989.
Liu et al., "A 650-pJ/bit MedRadio transmitter with an FIR-embedded phase modulator for medical micro-power networks (MMNs)", IEEE Transactions on Circuits and Systems I: Regular Papers, 2013, vol. 60, No. 12, pp. 3279-3288, DOI: 10.1109/TCSI. 2013.2265970.
Lo et al., "A fully integrated wireless SoC for motor function recovery after spinal cord injury", IEEE Transactions on Biomedical Circuits and Systems, Jun. 2017, vol. 11, Issue 3, pp. 497-509, first published May 23, 2017, DOI: 10.1109/TBCAS.2017.2679441.
Lo et al., "Bio-Impedance Characterization Technique with Implantable Neural Stimulator Using Biphasic Current Stimulus", Conference Proceedings of the IEEE Engineering in Medicine and Biology Society, 2014, pp. 474-477, doi: 10.1109/EMBC.2014.6943631.
Lonappan et al., "Nondestructive Measurement of Human Blood at Microwave Frequencies", Journal of Electromagnetic Waves and Applications, 2007, vol. 21, Issue 8, 1131-1139, DOI: 10.1163/ 156939307781749740.
Lopez-Lapena et al., "A closed-loop maximum power point tracker for subwatt photovoltaic panels", IEEE Transactions on Industrial Electronics, Mar. 2012, vol. 59, No. 3, pp. 1588-1596, DOI: 10.1109/TIE.2011.2161254.
Lu et al., "Flexible Neural Electrode Array Based-on Porous Graphene for Cortical Microstimulation and Sensing", Scientific Reports, Sep. 19, 2016, vol. 6, No. 33526, 9 pgs., DOI: 10.1038/srep33526.
Lu et al., "Ultra-flexible Piezoelectric Devices Integrated with Heart to Harvest the Biomechanical Energy", Scientific Reports, vol. 5, No. 16065, Nov. 5, 2015, 9 pgs. https://doi.org/10.1038/srep16065.
Lyu et al., "A 430-Mhz Wirelessly Powered Implantable Pulse Generator With Intensity/Rate Control and Sub-1 µA Quiescent Current Consumption", IEEE Transactions on Biomedical Circuits and Systems, vol. 13, No. 1, Feb. 2019, pp. 180-190, DOI: 10.1109/ TBCAS.2018.2879357.
Lyu et al., "A 915-MHz Far-Field Energy Harvester with -22-dBm Sensitivity and 3-V Output Voltage Based on Antenna-and-Rectified Codesign", IEEE Microwave and Wireless Components Letters, Aug. 2019, vol. 29, No. 8, pp. 557-559, DOI: 10.1109/LMWC. 2019.2923685.
Lyu et al., "A Multi-site Heart Pacing Study Using Wirelessly Powered Leadless Pacemakers", IEEE Xplore, Year: 2018, Date: Oct. 29, 2018 (retrieved on Jan. 15, 2020), 6 pgs.
Lyu et al., "An Energy-Efficient Wirelessly Powered Millimeter-Scale Neurostimulator Implant Based on Systematic Codesign of an Inductive Loop Antenna and a Custom Rectifier", IEEE Transactions on Biomedical Circuits and Systems, vol. 12, No. 5, Oct. 2018, pp. 1131-1143, DOI: 10.1109/TBCAS.2018.2852680.
Lyu et al., "Synchronized Biventricular Heart Pacing in a Closed-chest Porcine Model based on Wirelessly Powered Leadless Pacemakers", Scientific Reports, 10, Article No. 2067, 2020, 13 pgs.
Lyu et al., "Towards the Implementation of a Wirelessly Powered Dielectric Sensor with Digitized Output for Implantable Applications", IEEE Sensors Letters, Mar. 2019, vol. 3, No. 3, pp. 1-4, first published Jan. 30, 2019.
Mandal et al., "Low-power CMOS rectifier design for RFID applications", IEEE Transactions on Circuits and Systems I: Regular Papers, Jul. 2007, vol. 54, No. 6, pp. 1177-1188, DOI:10.1109/ TCSI.2007.895229.
Meyer et al., "First in a series on the leadless pacing: Percutaneous implantable transcatheter pacemaker—background, technical aspects, and possible pitfalls", e-Journal of Cardiology Practice, Aug. 23, 2016, vol. 14, No. 20, 18 pgs.
Mirbozorgi et al., "A Single-Chip Full-Duplex High Speed Transceiver for Multi-Site Stimulating and Recording Neural Implants", IEEE Transactions on Biomedical Circuits and Systems, vol. 10, No. 3, Jun. 2016, pp. 643-653, DOI: 10.1109/TBCAS.2015. 2466592.
Mirzavand et al., "High-Resolution Dielectric Sensor Based on Injection-Locked Oscillators", IEEE Sensors Journal, Jan. 1, 2018, vol. 18, Issue 1, pp. 141-148, published online published Nov. 13, 2017, DOI: 10.1109/JSEN.2017.2772923.
Montgomery et al., "Wirelessly powered, fully internal optogenetics for brain, spinal and peripheral circuits in mice", Nature Methods, 2015, vol. 12, No. 10, pp. 969-974, published online Aug. 17, 2015, DOI: 1031038/NMETH.3536.
Neimann et al., "Longevity of implantable pulse generators in bilateral deep brain stimulation for movement disorders", Neuromodulation: Technology at the Neural Interface, 2018, vol. 21, No. 6, pp. 597-603, DOI: 10.1111/ner.12923.

(56) References Cited

OTHER PUBLICATIONS

Pandey et al., "A Sub-100 µW MICS/ISM Band Transmitter Based on Injection-Locking and Frequency Multiplication", IEEE Journal of Solid-State Circuits, May 2011, vol. 46, Issue 5, pp. 1049-1058, first published Apr. 5, 2011, DOI: 10.1109/JSSC.2011.2118030.
Papotto et al., "A 90nm CMOS 5mb/s crystal-less rf transceiver for rf-powered wsn nodes", 2012 IEEE International Solid-State Circuits Conference, Feb. 19-23, 2012, pp. 451-453, DOI: 10.1109/ISSCC.2012.6177087.
Paul, "Inductance: loop and partial", John Wiley & Sons, 2011, 395 pgs., (presented in two parts).
Pellerano et al., "A mm-Wave Power-Harvesting RFID Tag in 90 nm CMOS", IEEE Journal of Solid-State Circuits, Aug. 2010, vol. 45, Issue 8, pp. 1627-1637, DOI: 10.1109/JSSC.2010.2049916.
Pozar, David M., "Microwave Engineering", John Wiley & Sons, Inc., Third Edition, 2005, Chapter 13 (Oscillators and Mixers): pp. 604-657, Chapter 14 (Introduction to Microwave Systems): pp. 658-708, 105 pgs.
Radiom et al., "Far-Field On-Chip Antennas Monolithically Integrated in a Wireless-Powered 5.8-GHz Downlink/UWB Uplink RFID Tag in 0.18-µm Standard CMOS", IEEE Journal of Solid-State Circuits, Sep. 2010, vol. 45, Issue 9, pp. 1746-1758, DOI: 10.1109/JSSC.2010.2055630.
Rahmani et al., "A 1.6mm3 Wirelessly Powered Reconfigurable FDD Radio with On-Chip Antennas Achieving 4.7 pJ/b TX and 1 pJ/b RX Energy Efficiencies for Medical Implants", Conference: 2020 IEEE Custom Integrated Circuits Conference (CICC), Apr. 2020, 4 pgs., DOI:10.1109/CICC48029.2020.9075935.
Rahmani et al., "A Dual-Mode RF Power Harvesting System With an On-Chip Coil in 180-nm SOI CMOS for Millimeter-Sized Biomedical Implants", IEEE Transactions on Microwave Theory and Techniques, Oct. 2018, vol. 67, No. 1, pp. 414-428, DOI:10.1109/TMTT.2018.2876239.
Rahmani et al., "A Wireless Power Receiver with an On-chip Antenna for Millimeter-size Biomedical Implants in 180 nm SOI CMOS", in 2017 IEEE MTT-S International Microwave symposium (IMS), Jun. 2017, pp. 300-303.
Rahmat-Samii et al., "Implanted antennas in medical wireless communications", Synthesis Lectures on Antennas, 2005, 1.1 pp. 1-82.
Rajavi et al., "An RF-powered FDD radio for neural microimplants", IEEE Journal of Solid-State Circuits, May 2017, vol. 52, Issue: 5, pp. 1221-1229, DOI: 10.1109/JSSC.2016.2645601.
Ramrakhyani et al., "Design and Optimization of Resonance-Based Efficient Wireless Power Delivery Systems for Biomedical Implants", IEEE Transactions on Biomedical Circuits and Systems, vol. 5, No. 1, Feb. 2011, pp. 48-63.
Randles, "Kinetics of rapid electrode reactions", Discussions of the Faraday Society, 1947, vol. 1, pp. 11-19.
Rategh et al., "Superharmonic Injection-Locked Frequency Dividers", IEEE Journal of Solid-State Circuits, Jun. 1999, vol. 34, No. 6, pp. 813-821.
International Preliminary Report on Patentability for International Application PCT/US2019/059657, Report dated May 25, 2021, dated Jun. 3, 2021, 8 Pgs.
International Preliminary Report on Patentability for International Application PCT/US2019/062443, Report dated May 25, 2021, dated Jun. 3, 2021, 7 Pgs.
International Preliminary Report on Patentability for International Application PCT/US2020/040283, Report dated Jan. 11, 2022, dated Jan. 20, 2022, 07 Pgs.
International Preliminary Report on Patentability for International Application PCT/US2020/041007, Report dated Jan. 11, 2022, dated Jan. 20, 2022, 06 Pgs.
International Preliminary Report on Patentability for International Application PCT/US2020/048001, Report dated Mar. 15, 2022, dated Mar. 31, 2022, 6 Pgs.
International Search Report and Written Opinion for Application PCT/US2021/35132, completed Aug. 2, 2021, dated Oct. 4, 2021, 10 pgs.
International Search Report and Written Opinion for International Application No. PCT/US2019/059657, Search completed Dec. 31, 2019, dated Jan. 21, 2020, 12 Pgs.
International Search Report and Written Opinion for International Application No. PCT/US2019/062443, Search completed Jan. 15, 2020, dated Jan. 29, 2020, 16 Pgs.
International Search Report and Written Opinion for International Application No. PCT/US2020/040283, Search completed Aug. 17, 2020, dated Sep. 28, 2020, 17 Pgs.
International Search Report and Written Opinion for International Application No. PCT/US2020/048001, Search completed Oct. 17, 2020, dated Nov. 20, 2020, 12 Pgs.
International Search Report and Written Opinion for International Application No. PCT/US2021/020343, Search completed Jun. 2, 2021, dated Jun. 22, 2021, 13 Pgs.
International Search Report and Written Opinion for International Application No. PCT/US2021/073036, Search completed Apr. 14, 2022, dated May 3, 2022, 18 Pgs.
International Search Report and Written Opinion for International Application PCT/US2017/0047901, filed Aug. 22, 2017, 13 pgs.
International Search Report and Written Opinion for International Application PCT/US2017/052163, filed Sep. 19, 2017, 13 pgs.
International Search Report and Written Opinion for International Application PCT/US2020/049349, dated Nov. 24, 2020, 7 pgs.
International Search Report and Written Opinion for International Application PCT/US2021/21467, dated Jun. 3, 2021, 8 pgs.
International Search Report for International Application No. PCT/US2020/041007; Search completed Aug. 29, 2020, dated Oct. 2, 2020, 13 pgs.
Abiri et al., "Inductively powered wireless pacing via a miniature pacemaker and remote stimulation control system", Science Reports, vol. 7, No. 6180, Jul. 21, 2017. pp. 1-10, doi: 10.1038/s41598-017-06493-5.
Agarwal et al., "A 4µW, ADPLL-Based Implantable Amperometric Biosensor in 65nm CMOS", 2017 Symposium on VLSI Circuits, Kyoto, Japan, 2017, pp. C108-C109. doi: 10.23919/VLSIC.2017.8008566.
Ahn et al., "Optimal Design of Wireless Power Transmission Links for Millimeter-Sized Biomedical Implants", IEEE Transactions on Biomedical Circuits and Systems, Jan. 20, 2015, vol. 10, Issue 1, pp. 125-137, DOI: 10.1109/TBCAS.2014.2370794.
Arfin et al., "An energy-efficient, adiabatic electrode stimulator with inductive energy recycling and feedback current regulation", IEEE Transactions on Biomedical Circuits and Systems, Feb. 2012, vol. 6, Issue 1, pp. 1-14, first published Oct. 6, 2011, DOI: 10.1109/TBCAS.2011.2166072.
Atzori et al., "The Internet of Things: A survey", Computer Networks, Oct. 2010, vol. 54, Issue 15, pp. 2787-2805, https://doi.org/10.1016/j.comnet.2010.05.010.
Bahrami et al., "Flexible, polarization-diverse UWB antennas for implantable neural recording systems", IEEE Transactions on Biomedical Circuits and Systems, vol. 10, No. 1, Feb. 2016, pp. 38-48.
Extended European Search Report for European Application No. 19887763.1, Search completed Jul. 11, 2022, dated Jul. 19, 2022, 07 Pgs.
International Search Report and Written Opinion for International Application No. PCT/US2022/071066, Search completed Jun. 21, 2022, dated Jul. 5, 2022, 21 Pgs.
Cogan et al., "Potential-biased, asymmetric waveforms for charge-injection with activated iridium oxide (AIROF) neural stimulation electrodes", IEEE Transactions on Biomedical Engineering, vol. 53, No. 2, Feb. 2006, first published Jan. 23, 2006, pp. 327-332, doi: 10.1109/TBME.2005.862572.
Daubert et al., "2012 EHRA/HRS expert consensus statement on cardiac resynchronization therapy in heart failure: implant and follow-up recommendations and management", Heart Rhythm, vol. 9, No. 9, Sep. 1, 2012, pp. 1524-1576, doi: 10.1016/j.hrthm.2012.07.025.
Li et al., "Parylene-based integrated wireless single-channel neurostimulator", Sensors and Actuators A: Physical, vol. 166, Issue 2, Apr. 2011, pp. 193-200, https://doi.org/10.1016/j.sna.2010.03.003.

(56) References Cited

OTHER PUBLICATIONS

Niemann et al., "Longevity of Implantable Pulse Generators in Bilateral Deep Brain Stimulation for Movement Disorders", Neuromodulation, vol. 21, No. 6, Aug. 2018, published online Dec. 19, 2017, pp. 597-603, doi: 10.1111/ner.12743.

Rahmani et al., "An Integrated Battery-Less Wirelessly Powered RFID Tag with Clock Recovery and Data Transmitter for UWB Localization", Microwave, MTT-S International Symposium, Aug. 4-6, 2020, Los Angeles, CA, USA, pp. 460-463, DOI: 10.1109/IMS30576.2020.9223821.

Sun et al., "A two-hop wireless power transfer system with an efficiency-enhanced power receiver for motion-free capsule endoscopy inspection", IEEE Transactions on Biomedical Engineering, vol. 59, No. 11, Nov. 2012, published online Jun. 29, 2012, pp. 3247-3254. doi: 10.1109/TBME.2012.2206809.

Sun et al., "Wirelessly powered implantable pacemaker with on-chip antenna", 2017 IEEE MTT-S International Microwave Symposium (IMS), Jun. 4-9, 2017, pp. 1242-1244, DOI: 10.1109/MWSYM.2017.8058831.

Extended European Search dated Jul. 19, 2022, issued in related European Application No. 19887763.1, 7 pgs.

International Preliminary Report on Patentability dated Sep. 22, 2022 issued in related International Application PCT/US2021/021467, 6 pgs.

\* cited by examiner

PERFORMANCE SUMMARY AND COMPARISON WITH STATE-OF-THE-ART AREA-CONSTRAINED TRANSCEIVERS

| | | This Work | CICC '20 [17] | JSSC '17 [21] | JSSC '17 [22] | JSSC '16 [19] | TBioCAS '16 [20] |
|---|---|---|---|---|---|---|---|
| | Technology | 180nm CMOS | 180nm SOI CMOS | 65nm CMOS | 40nm CMOS | 180nm CMOS | 180nm CMOS |
| | Radio Type | Active FDD | Backscatter TDD | Active FDD | Active FDD | Active FDD | Active FDD |
| | Powering Method | Wireless/ RF @ 250 MHz | Wireless/ RF @ 27 MHz | Wireless/ Ultrasound @ 1 MHz | Probed/ RF @ 1.85 GHz | Battery | Wireless/ RF @ 13.56 MHz |
| TX | Frequency (GHz) | 4.12 | 0.700 | 0.0025 | 1.75 | 0.112 | 3.1-7 |
| | Modulation type | UWB OOK | LSK | OOK | RZ-OOK | PPM | OOK, OOK-BPSK |
| | Max. data rate (Mbps) | 150 | 27 | 0.1 | 58 | 2 | 500 |
| | Comm. distance (cm) | 18 | 0.1-0.25 | 6 | 5* | 50 | 15 |
| | Power cons. (mW) | UWB: 0.698 @150 Mbps, OOK: 1.87 | <2.7 | <0.177 | 0.093 | <13.6 | OOK: 3.5, OOK-BPSK: 5.4 |
| | Max. energy eff. (pJ/b) | 4.7 | 103 | NA | 1.6 | NA | 10.8 |
| | BER | <10⁻⁴ | <10⁻⁴ | NA | NA | NA | <10⁻⁵ |
| RX | Frequency (MHz) | 250 | 700 | 1 | 1850 | 49.86 | 2400 |
| | Modulation type | ASK | ASK | OOK | ASK | OOK | OOK |
| | Max. data rate (Mbps) | 2.5 | 0.00066 | 0.025 | 2.5 | 0.1 | 100 |
| | Power cons. (µW) | 2.6 | <2.7 | NA | 7.2 | 36 | 5000 |
| | Max. energy eff. (pJ/b) | 1.0 | NA | NA | 2.9 | 360 | 50 |
| | Comm. distance (cm) | 1 | 0.1-2.5 | 6 | 5* | 20 | 15 |
| | BER | <10⁻⁴ | NA | <10⁻⁴ | 5.4×10⁻⁵ | 10⁻³ | 10⁻³ |
| | Off-Chip Components | No | No | US transducer ×2, cap | Duplexer | Battery, magnetic antenna | Coils ×3, Ant. match. cap. |
| | Volume (mm × mm × mm) | 2.4×2.2×0.3 | 2.5×2×0.015** | 2.6×6.5×1.8 | 2×1.6×0.6 | 10×1×1 | 30×10×1* |

FIG. 21

INTEGRATED ENERGY HARVESTING TRANSCEIVERS AND TRANSMITTERS WITH DUAL-ANTENNA ARCHITECTURE FOR MINIATURIZED IMPLANTS AND ELECTROCHEMICAL SENSORS

CROSS REFERENCE TO RELATED APPLICATION

This application is a continuation of PCT Patent Application No. PCT/US2021/020343, entitled "Integrated Energy Harvesting Transceivers and Transmitters With Dual-Antenna Architecture for Miniaturized Implants and Electrochemical Sensors" to Babakhani et al., filed Mar. 1, 2021, which claims priority to U.S. Provisional Application No. 63/136,096, entitled "Wirelessly Powered Chemical/PH Sensor with Integrated Radio and Power" to Babakhani et al., filed Jan. 11, 2021 and U.S. Provisional Application No. 62/983,494, entitled "Integrated Energy Harvesting Transceiver Based on a Dual-Antenna Architecture for Miniaturized Implants" to Yu et al., filed Feb. 28, 2020 the disclosures of which are incorporated herein by reference in their entirety.

STATEMENT OF FEDERALLY SPONSORED RESEARCH

This invention was made with government support under Grant Number 1533688, awarded by the National Science Foundation and Grant Number DE-FE0031569, awarded by the U.S. Department of Energy. The government has certain rights in the invention.

FIELD OF THE INVENTION

The present invention relates to wirelessly powered transceivers and transmitters, specifically to small form-factor transceivers and transmitters achieving high energy efficiency and data throughput while staying as small as possible, which can be used for biomedical implants and/or electrochemical sensors in environmental applications.

BACKGROUND OF THE INVENTION

Emerging applications of biomedical and industrial/environmental sensor devices have shown an ever-increasing demand for data acquisition with higher bandwidth and a higher resolution. For instance, research on the anatomical, physiological, and computational bases of human cognitive and motor functions has made important strides in recent years, yet has been limited by a glaring lack of information on the dynamics of processes. This is a methodological limitation related to the low spatial and temporal resolution of widely available tools such as fMRI, EEG, behavioral, and stroke lesion-based approaches. Today, neural interface implantable systems are becoming increasingly popular as they have demonstrated great potentials in novel diagnostic and treatment methods. They are used in a variety of applications such as Brain-Machine Interface (BMI) systems, cochlear implants, and retinal prosthesis. To address clinical constraints and alleviate infection risks, wireless operation is a necessity for human implantable systems. Therefore, commercial implants utilize either batteries or inductive coupling through a pair of coils for powering the internal electronics. Also, bidirectional data transmission is conducted through a wireless link that utilizes electromagnetic (EM) antennas.

Electrochemical sensors are a crucial element which can translate the environmental condition in which the sensor is placed in, to an electrical signal. Because of this property, electrochemical sensors have been used in many different applications such as, environmental monitoring, food monitoring, medical diagnostics etc. One of the forms of electrochemical sensing is the measurement of pH (Potential hydrogen) using a pH electrode, which translates the activity of hydrogen ions in a chemical solution to an electrical potential. When two solutions with different Hydrogen activities are separated by a glass membrane, it produces a potential difference across the membrane which can be translated to a pH value governed by equation (1), where pH(X) pH of unknown solution, pH(S)=7, Es≡Electric potential of reference electrode, Ex≡Electric potential of working electrode, F≡Faraday constant, R≡Universal gas constant, T≡Temperature in Kelvin. This equation is derived from the Nernst equation and the Nernst equation is the backbone of electrochemical sensors as it describes the potential of electrochemical cells to the concentration of ions taking place in the reaction.

$$pH(X) = pH(S) + \frac{(E_S - E_X)F}{RT\ln(10)} \quad (1)$$

With the ongoing improvements in solid-state electronics and its fabrication methodologies, form factors for electrochemical sensors have become exponentially smaller. Not only that, but among the analytical strategies to monitor environmental conditions, quality of pharmaceuticals, and to perform medical diagnostics, electrochemical sensors are advantages due to its low cost, fast and selective analysis. The solution pH in which the electrochemical sensor is submerged in greatly affects the performance of the sensor itself. Therefore, pH measurement is a crucial component for electrochemical analysis.

Recent advances in semiconductor technology have resulted in a significant integration capability and size reduction of electronics. However, the overall size of a transceiver is not scaled with the same rate since it is dominantly controlled by the size of the required components for power and data communication. Battery-powered devices cannot be made smaller than a few centimeters since the power density of state-of-the-art batteries fails to address the demands of long-term miniaturized implants. On the other hand, the efficiency of power transfer systems is proportional to the dimension of power receiver and transmitter structures. Compared with traditional inductively coupled Wireless Power Transfer (WPT) systems that utilize cm-sized structures, high-frequency WPT systems can incorporate mm-sized antennas at the cost of a lower efficiency.

BRIEF DESCRIPTION OF THE DRAWINGS

FIG. 21 shows a summary of performance of a wirelessly powered FDD radios in accordance with several embodiments of the invention.

SUMMARY OF THE INVENTION

Figure 1:
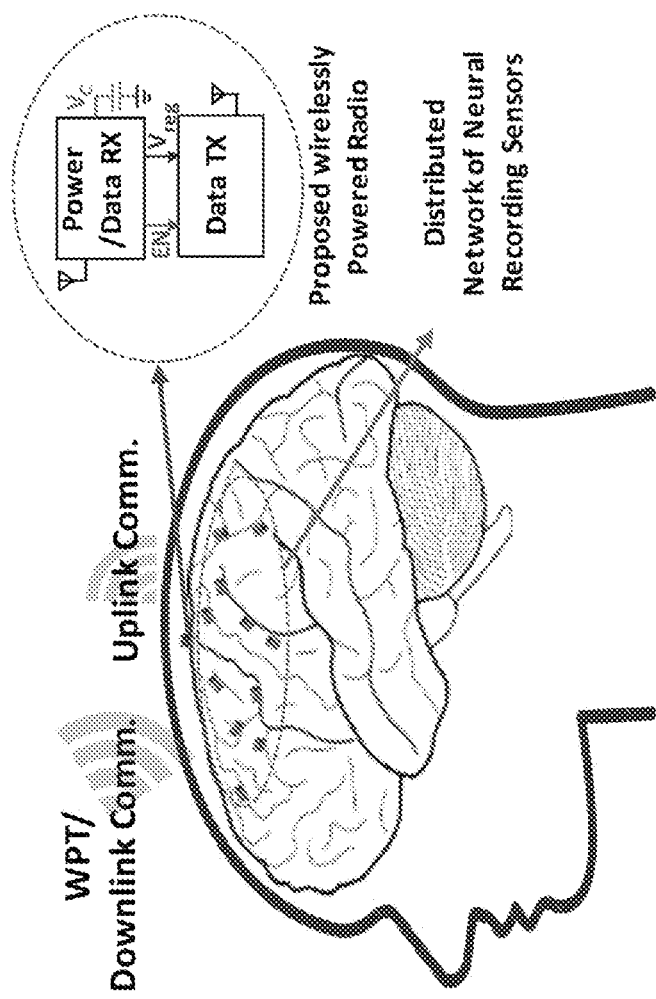
FIG. 1 conceptually illustrates an example of a closed-loop neural recording and stimulation system in accordance with some embodiments of the invention.

Rising demand for continuous monitoring of human body and healthcare devices in recent years has resulted in the development of implantable devices. Infection risks and mobility concerns constrain implants to operate without any transcutaneous wire connection, which raises serious challenges for powering and data telemetry. In addition, lack of information on many physiological processes such as human cognitive and motor functions has hindered research on bases of the processes and it mainly stems from available measurement systems limitations. An objective of the present disclosure is to investigate, develop, and demonstrate new millimeter-sized (mm-sized) integrated implantable devices that tackle the challenges associated with Wireless Power Transfer (WPT) through biological tissues and ultra-low power data transceivers.

Previous works with an on-chip antenna typically only target continuous power delivery with a power budget limited to hundredths of microwatts. Such low capability cannot power circuits such a neural recording device. An on-chip capacitor may be used, but this can still only deliver milliwatts of power for short periods of power and not continuously.

Several embodiments of the invention include a wirelessly powered data transceiver integrated on a CMOS technology that is wirelessly powered through an inductive link. To ease the encapsulation process, improve reliability, and eliminate need for any post-fabrication process, the entire system, including antennas for power delivery and communications, can be designed on a silicon chip accordingly to many embodiments of the invention. The development of this system enables a new generation of closed-loop recording and stimulation systems for the human brain which opens a new gate toward human brain mapping and treating different brain-related disorders.

One of the main requirements of future neural implants is improving the spatio-temporal resolution of the recorded signals to provide more insight into the complex mechanism of human functions. To enable recording at a fine scale, many embodiments of the invention utilize implantable System-on-Chips (SoCS) to realize a distributed neural recording system. The system-level requirements of such SoCS are long-term wireless operation, mm-sized form-factor, and integration capability on a commercial CMOS process to make them scalable and cost-efficient. Miniaturizing the size of an implant is a key step for fulfilling the needs of next-generation implantable systems since it results in a higher sensor density and also enables signal recording at an ultra-small structural scale. FIG. 1(a) shows a conceptual multi-site and distributed neural system enabled by multiple mm-sized recording/stimulating units. Each unit contains a data transceiver (TRX) that is placed on top of a microelectrode array. Thanks to their compact size, individual units can be tightly placed on the brain and to improve the recording resolution. There are many challenges toward realizing a practical neural interface system. In particular, the following discussion focuses on the data communication problem and proposes a TRX compatible with the system-level requirements of next-generation implantable systems. Each TRX acts as a communication hub between the electrodes within a unit and an external reader. Recent neural recording systems have reported up to 4096 recording electrodes. On the other hand, various recording methods such as ECoG or spike recording demand different sampling rates that may reach as high as 10 ksps per channel. Hence, the overall communication bandwidth may exceed tens of Mbps.

A practical TRX should support the demanded bandwidth and be compatible with all of the system-level requirements of miniaturized implants. Achieving such a high data rate is extremely difficult due to severe power budget constraints and poor performance of electrically small antennas used for power harvesting and data communication. Considering the Specific-Absorption-Rate (SAR) limit of various biological tissues and non-idealities of a WPT system such as coil misalignment and link variations, the maximum harvested power by mm-sized power harvesters is about few hundreds of micro-Watts. Moreover, the wavelength of EM waves at the frequencies that data communication is typically conducted ranges from tens to hundreds of centimeters. A mm-sized antenna is often much smaller than the wavelength and has a poor radiation efficiency. Therefore, an ideal TRX for mm-sized implants should achieve a very high energy efficiency to support high data rates.

Backscattering is a widely adopted technique for telemetry in implantable applications since it results in extremely low power consumption. The transmitted data pattern can be used for Load Shift Keying (LSK) modulation of the power coil which alters the reflected signal to an external reader. Despite achieving a superior energy efficiency over active communication, backscattering radios fail to address the main requirements of mm-sized implants. Due to the small size of the power coil and a strong power carrier, that acts as a blocker, detection of the reflected signal on the reader side may be difficult or even impossible. In addition, modulating the power coil disrupts the power flow into the system and degrade power transfer efficiency. Furthermore, the communication bandwidth of backscattering radios is often very low due to the high quality factor (Q) of the power coil that limits the data rate, consequently.

Active TRXs do not face the fundamental challenges of their backscattering counterparts and can potentially achieve high data rates at the expense of higher power consumption. Considering the stringent power budget in implantable applications, the main design goal is achieving the highest possible energy efficiency; and proper modulation schemes should be chosen. It is well known that there is a trade-off between energy efficiency and spectral efficiency in communication systems. Narrow-band modulation schemes demand a relatively complex architecture to generate an accurate frequency whereas wide-band modulation schemes such as On-Off Keying (OOK) have often less complexity and result in higher energy efficiency.

Many embodiments of the invention described here present the design, implementation, and verification of a fully integrated and RF-powered wireless data TRX. The proposed radio achieves the state-of-the-art energy efficiency and the smallest form-factor compared with prior art mm-sized wirelessly powered active radios. The system can implemented on a single CMOS silicon chip and all required components for power delivery, energy storage, and data communication, including an on-chip coil and a dipole antenna, can be implemented on the same chip. In other embodiments, some components such as antennas can be located off chip. The TRX is designed to enable simultaneous power delivery and data communication through two distinct wireless links separated in the frequency domain. The design supports data rates of up to 2.5 Mbps in the receiver and data rates of up to 150 Mbps in the transmitter chain, respectively. In one embodiment, the implemented system occupies a total area of 2.4×2.2×0.3 mm3 without any substrate thinning and features a fully on-chip integration that potentially results in cost reduction, elimination of any post-fabrication process, and reliability improvement.

DETAILED DISCLOSURE OF THE INVENTION

Turning now to the drawings, integrated energy harvesting transceivers based on dual-antenna architecture for miniaturized implants in accordance with the embodiments are disclosed.

As previously mentioned, there is a methodological limitation related to the low spatio-temporal resolution of widely available tools such as fMRI, EEG, behavioral, and stroke lesion-based approaches. On the other hand, intracranial-electroencephalographic (icEEG) signal recording successfully has yielded valuable insight into the ultra-small structural scale of the human brain.

An example of a closed-loop neural recording and stimulation system in accordance with embodiments of the invention is illustrated in FIG. 1(a), where neural signals are recorded by one or more implanted devices and transferred to an external receiver. Due to safety and infection concerns, there is no transcutaneous wire connection between an implantable device and external equipment, and the communication is wireless. This provides challenges for powering the system and data communication. Emerging applications of Implantable Medical Devices (IMDs), such as Brain Machine Interface (BMI) demand biological signal acquisition with a high data rate and a high spatial resolution. Therefore, development of a robust neural implantable device is a key step toward building a practical closed-loop system that can be used for clinical purposes. To mitigate requirements of an advanced neural interface system, next generation IMDs should be miniaturized, wireless, and low-power.

Miniaturization is a key feature of IMDs since it is a solution to improve spatio-temporal resolution of recorded signals. It can lead to a higher sensor density and enable signal recording at an ultra-small structural scale. In addition, smaller implants cause less damage to living tissues, ease the encapsulation process, and are easier to implant. For the sake of miniaturization, batteries may not be used for powering implanted devices because of their large form-factor. In addition, batteries have limited lifetime and are not a reasonable solution for powering IMDs that are implanted via a surgical procedure. Fortunately, energy harvesting methods can be a promising approach for powering small IMDs.

In many embodiments of the invention, electromagnetic waves provide a source of power and energy is wirelessly transferred to the system. As will be described below, a system in accordance with embodiments of the invention may include multiple analog and RF front-end blocks that are provide power extraction, sense neural signals and digitization, and transfer information to and form an external transceiver. Such systems incorporate the fields of ultra-low power, high-frequency and high-speed integrated circuits, and wireless energy transfer techniques.

Integrating the entire system, including the power harvesting module and antennas, in a CMOS die is an elegant solution for improving the reliability of an IMD and reducing overall cost and form-factor of the system. On the other hand, the IMD should be able to communicate information with a relatively high data-rate to enable real-time monitoring and decoding of human cognitive functions. Given the challenges imposed by wireless power delivery to a millimeter-sized IMD, data communication with a high rate is challenging as well as designing a low-power and efficient data transceiver. Systems described here in accordance with embodiments of the invention provide millimeter-sized IMDs for closed-loop neural recording and stimulation with a focus on power harvesting platform and low-power data transceiver.

Data communication is one of the most critical tasks that dominates the overall performance of an implant. Thus, the research trend in medical applications is focused on wirelessly powered transceivers (TRX) with small form-factors and high efficiencies. Passive radios that are based on backscattering are superior to their active counterparts in terms of energy efficiency. However, they cannot meet the requirements of a high-performance implant due to limited data-rate (DR) and operating range. Recently, active radios have been reported with >1 Mbps DR and >5 cm operating range. Off-chip components that are used for power delivery and data communication have limited their integration capability and there is still a significant need for developing an integrated TRX with a mm-sized form-factor and satisfying DR. Many embodiments of the invention provide a mm-sized reconfigurable radio that integrates all required components for power delivery and data communication on a single silicon chip.

Several embodiments include a 2.4×2.2×0.3 mm$^3$ wirelessly powered TRX with on-chip antennas for power delivery and data communication. The TRX can receive power and downlink (DL) communication data through a near-field Radio Frequency (RF) link and conduct uplink (UL) data communication with a separate on-chip antenna connected to a transmitter (TX) operating at a different frequency than the power link. FIG. 1($a$) highlights the motivation for the development of a miniaturized TRX where the proposed radio is used as a communication hub in a distributed neural recording and stimulation sensor network. Due to the small form-factor and the fact that the on-chip antennas eliminate the need for any post-fabrication process the proposed radio is a viable solution for area-constrained biomedical implants. Several embodiments of the invention focus on circuit design challenges of an ultra-low power radio that is compatible with the requirements of implantable devices. A goal is to achieve energy-efficient data communication in both RX and TX chains to enable high-data-rate wireless communication under severely restricted power budgets rendered by a mm-sized power harvesting system. Data modulation schemes and TRX architecture are carefully chosen to minimize circuit complexity and overall power consumption.

In further embodiments of the invention, the transceiver includes a pH sensor and can transmit a signal indicative of a detected pH level. Several types of electrochemical sensors that can be produced in the micrometer scale. Ion-sensitive field effect transistors (ISFET) and microelectrodes are such examples of micrometer-scaled electrochemical sensors that may be utilized in accordance with embodiments of the invention. A circuit that is sensitive enough to be able to read the signals generated from these electrochemical sensors can significantly reduce the form factor, fabrication cost, and time of the overall electrochemical sensing system. In many embodiments of the invention, a multi-electrode array (MEA) microelectrode for glutamate detection is used. Microelectrodes can be used as a pH electrode with a Platinum (Pt) working electrode and an iridium oxide (IrOx) reference electrode. Voltage dependance of the electrode to a changing pH solution is recorded to be −77.5 mV/pH. Therefore, this electrode is able to be used as a pH electrode for a wirelessly powered pH sensor system in accordance with embodiments of the invention.

To enable a transceiver to meet severe power constraints, many embodiments of the invention utilize one or more of the following techniques: 1) Co-optimizing the on-chip coil (OCC) and the wireless link with power harvesting circuitry to maximize power transfer efficiency. 2) Exploiting a power management unit (PMU) to set the operating mode and biasing condition of different blocks depending on the available power and power consumption of the system. 3) Utilizing a dual antenna architecture to minimize the interference between power link and transmitter. 4) Exploiting amplitude-based modulation schemes in the transmitter for maximizing energy efficiency. 5) Utilizing a transmitter block architecture based on a power oscillator (PO) to achieve the highest possible energy efficiency. 6) Applying circuit-level power reduction techniques in the PO design. 7) 3) Stacking MOSCAP and MIM capacitors to achieve a high density and realize a ~5 nF on-chip capacitor for energy storage.

System Architecture

Figure 2:
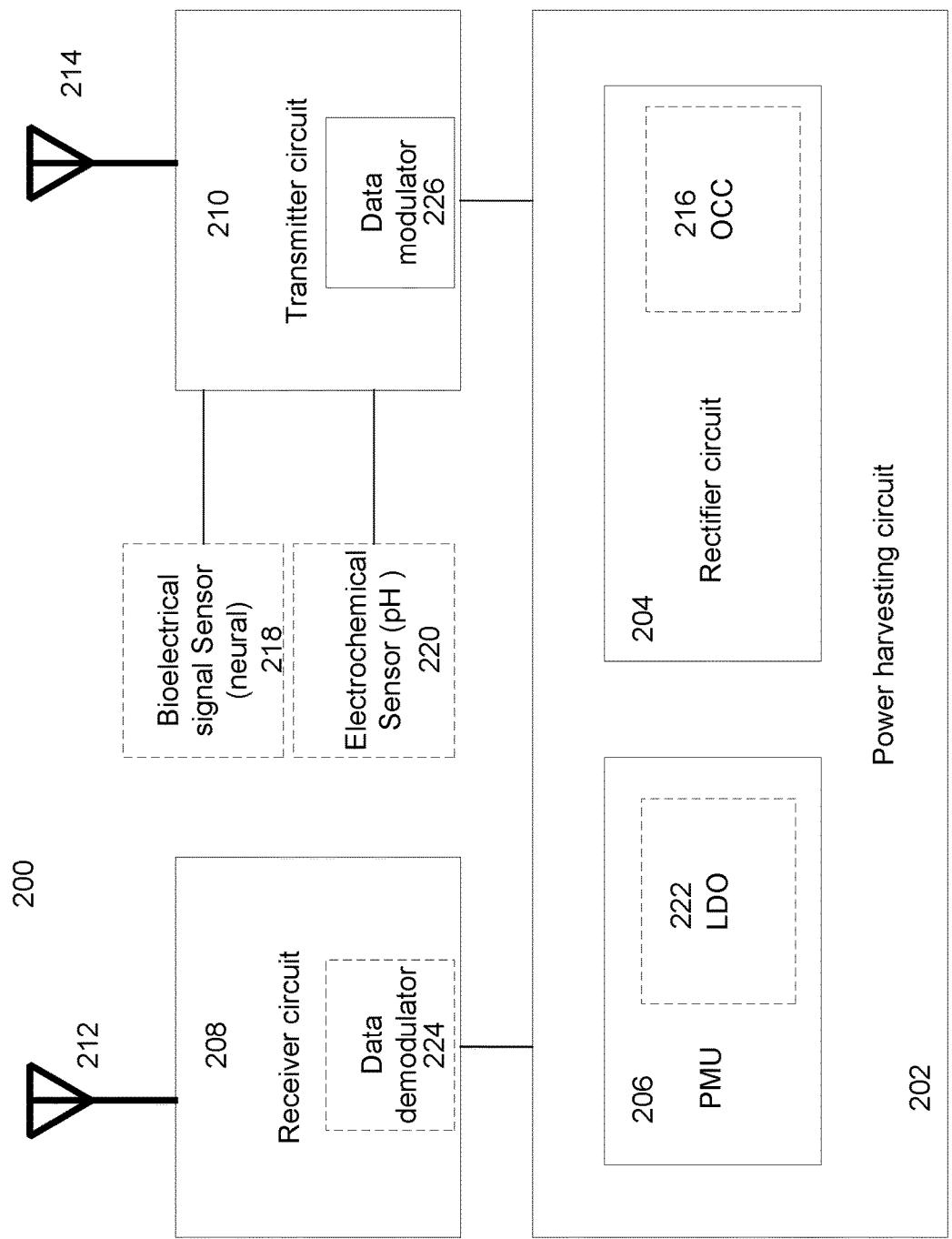
FIG. 2 conceptually illustrates a block diagram of a small form factor, high frequency wirelessly powered transceiver system in accordance with several embodiments of the invention.

A block diagram of a transceiver system in accordance with several embodiments of the invention is depicted in FIG. 2. The transceiver system 200 includes a power harvesting system 202, which includes a rectenna (rectifier circuit) 204 and a power management unit (PMU) 206, a receiver circuit (RX) 208, and a transmitter circuit (TX) 210. A receive antenna 212 is connected to the receiver circuit 208 and a transmit antenna 214 is connected to the transmitter circuit 210.

The rectenna 204, which may include an on-chip coil (OCC) 216, four full-wave rectifiers and a matching capacitor, can receive energy through an inductive link and convert RF energy into a DC voltage. The OCC can be shared between the power harvesting system 202 (for power) and the receiver 208 (for receiving data). The converted power by the rectenna can be used to power other components of the transceiver system 200 such as the data transmitter.

The receiver circuit 208 may include a data demodulator 224 to receiver data at the transceiver system. Some embodiments may not receive data and therefore may not have a data decoder in the receive circuit. Some embodiments may extract a clock signal from the received signal. In some embodiments, the receive antenna 212 is a loop antenna with a capacitor to utilize resonance inductive coupling. In other embodiments, the receive antenna 212 is a dipole antenna and other configurations maybe contemplated.

In several embodiments, the transmitter 210 includes a reconfigurable data modulator circuit 226 to send data out from the system, as will be discussed further below. In different embodiments of the invention, the transmit antenna 214 can be a monopole, dipole, or loop antenna as appropriate to a particular application, although isolation from the receive antenna 212 is desirable.

The main power-consuming block of the system is often the transmitter (TX) 210. Due to the challenges of power transfer to mm-sized implants, harvested power is often less than the instantaneous power consumption of the TX block 210. Therefore, power management unit (PMU) 206 can duty-cycle the operation of the data TX 210 to maintain a minimum voltage across the storage capacitor ($C_S$) and establish charging and discharging modes for $C_S$. In charging mode, the converted power by the rectenna increases the voltage level across $C_S$ ($V_C$) until the PMU 206 activates the TX block 210. PMU 206 and data receiver (RX) 208 blocks can be active during the entire operation and constituent sub-circuits are designed in subthreshold region to maximize sensitivity and reduce the charging time ($t_{charge}$) of $C_S$. On the other hand, discharging time ($t_{discharge}$) of $C_S$ is proportional to the capacitance value; hence using a large capacitance enables the PMU to follow rapid transitions of $V_C$. In several embodiments of the invention, in order to achieve a high capacitance density, MIM capacitors (2 fF/μm2) are stacked over MOSCAP devices (5.5 fF/μm$^2$) to realize a 5 nF capacitor, although other designs may be utilized to achieve a target capacitance. The transition from charging mode to discharging mode represents a significant load variation for the low dropout voltage regulator (LDO) 222 in the PMU 206. To ensure the regulator remains functional, the bandwidth of the error amplifier can be increased at the onset of active mode. The PMU 206 can adaptively change the bias condition of the LDO and enables it to maintain a constant voltage at its output.

In several embodiments of the invention, a transceiver for a neural recording application (e.g., neural stimulation) can receive information from a bioelectrical signal sensor 218. A bioelectrical signal sensor 218 can include any of a variety of biosensors and neural sensors, such as, but not limited to, neural LFP (local field potential), electrocardiogram (ECG), compound action potential, electromyogram (EMG), Electroencephalogram (EEG), Electromyogram (EMG), Electrooculogram (EOG), Electroretinogram (ERG), and/or Electrogastrogram (EGG). Such sensors may sense electrical signals, potential, or other characteristics in a variety of ways such as the difference between two electrodes, electrical resistance, or the magnetic field induced by electrical currents. Such neural recording applications may complement neural stimulation for a variety of therapies, such as pain control. As will be explained further below, the voltages and frequency (ranging from few Hz to kHz) may be selected for noise purposes and to reject DC frequencies.

In some other embodiments of the invention, a transmitter for electrochemical sensing can include an electrochemical sensor 220, such as a pH sensor. Such sensors may be used in industrial or environmental applications, and such configurations are discussed further below.

In many embodiments, a 250 MHz signal is utilized to power the chip by received signal as it provides high penetration, and higher harmonics of this frequency can cause interference. Additionally, the received power signal may utilize amplitude modulation. In several embodiments, a 4.15 GHz center frequency is utilized for the transmit signal to provide high bandwidth and avoid harmonics of the receiver frequency. Frequencies should be utilized that are far from each other to be more isolated and decouple interference between the receive power link and the transmit uplink. A system in accordance with embodiments of the invention may adaptively set transmit mode and/or data rates and utilize variable power, rather than target a specific power budget and data rate.

Figure 2A:
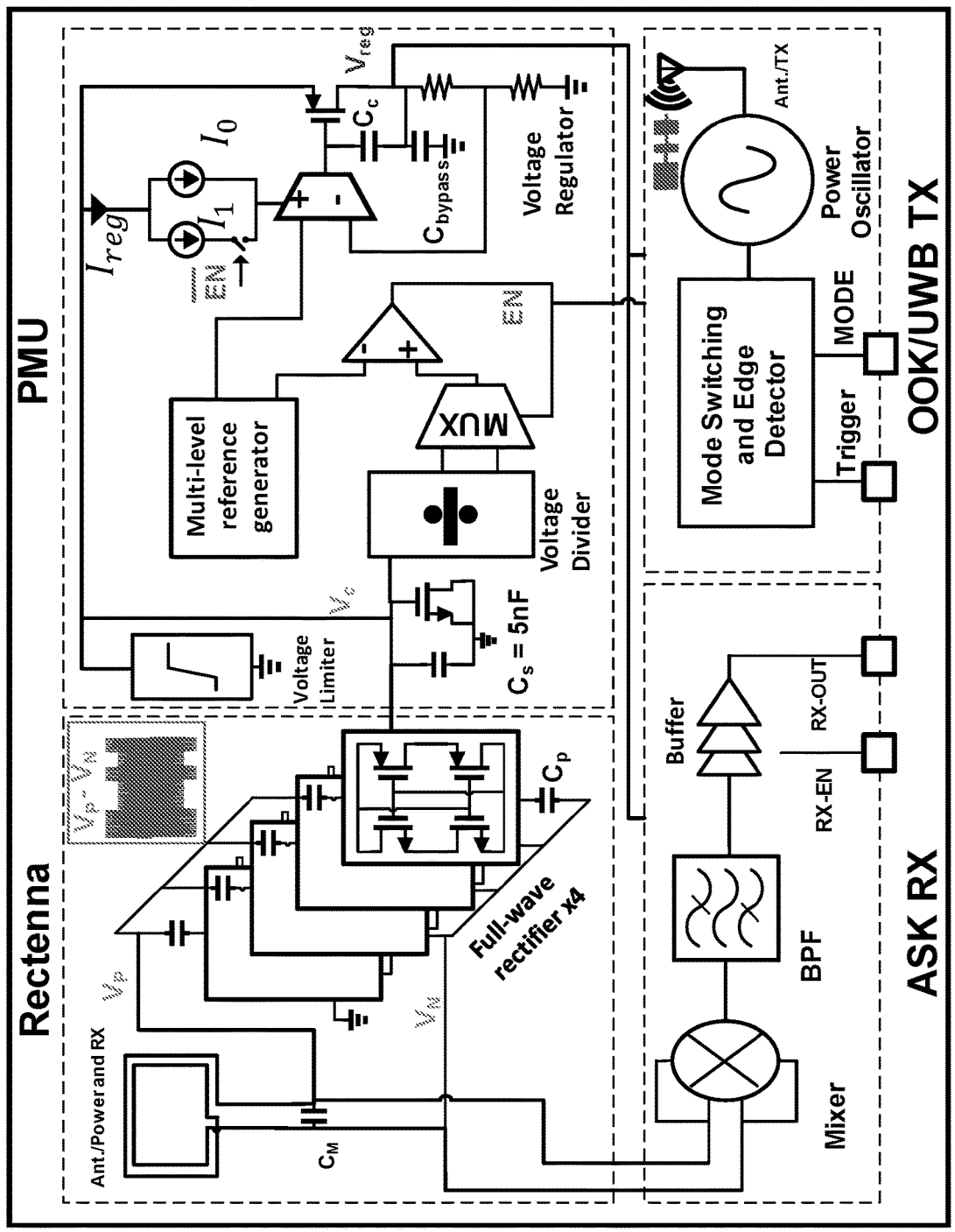
FIG. 2A conceptually illustrates a block diagram of another small form factor, high frequency wirelessly power transceiver in accordance with several embodiments of the invention.

FIG. 2A conceptually illustrates to components of a wireless powered transceiver system in accordance with embodiments of the invention, which are discussed in greater detail below. Although specific transceiver systems are described above with respect to FIGS. 2 and 2A, one skilled in the art would recognize that certain components of the system described above may be different, may have different characteristics, or be different in number in accordance with embodiments of the invention as appropriate to a particular application. Further discussion of circuit designs that may be utilized for power management, power harvesting and transfer, and frequency selection and optimization of a wireless link can be found in "A Dual-Mode RF Power Harvesting System With an On-Chip Coil in 180-nm SOI CMOS for mm-Sized Biomedical Implants" by Hamed Rahmani and Aydin Babakhani (October 2018, IEEE Transactions on Microwave Theory and Techniques), the relevant portions of which are incorporated by reference.

Wireless Communication

The required data rate of transmitter circuitry (TX) and (RX) paths in medical implants and industrial/environmental sensors varies considerably and thus the communication is typically asymmetric. The wireless link from an external reader to the RX, which can be referred to as downlink (DL), typically has a data rate that does not exceed a few Mbps. On the other hand, the wireless link from the TX to an external reader, which can be referred to as uplink (UL), typically has a large bandwidth to support data rates up to hundreds of Mbps. In other embodiments of the invention, the transceiver does not need to receive data in a downlink channel and may only utilize the received signal for power and/or clock signal.

In many embodiments that receive data via downlink, the data is incorporated into the received signal with an Amplitude-Shift-Keying (ASK) modulation scheme. The RX block 208 can be directly powered by the power harvesting system 202 and may be active during the entire operation of the system. Hence it can be important to minimize the overall power consumption of the RX 208. To enable simultaneous UL and DL communication, several embodiments utilize Frequency Division Duplexing (FDD) for transmitting UL and set the center frequency in the GHz region. Such a high center frequency alleviates the undesired effects of the strong power link on the TX communication and minimizes the interference of UL and DL. Besides, the efficiency of a mm-sized antenna improves as the frequency increases to the GHz region. In many embodiments, the UL communication incorporates amplitude-based modulation schemes due to their superior energy efficiency and less sensitivity to supply variation as opposed to frequency-based modulation schemes. In various embodiments of the invention, the TX block 210 can be configured to transmit UL data with either OOK or Ultra-Wideband (UWB) modulation.

The PMU 206 can convert the unregulated output voltage of the rectifier to a constant DC voltage and adjusts the power consumption of the entire system. The maximum harvested power in mm-sized implants is often less than the power consumption of a power-hungry block such as a data TX 210. One technique to tackle this problem is duty-cycling the operation of power-demanding blocks and lowering the overall power consumption of the system. Depending on the power consumption of each block, the PMU 206 can set its power delivery scheme to either continuous or duty-cycled. A storage capacitor ($C_S$) is used for storing the converted energy by the rectifier and a voltage limiter is included in the PMU 206 to prevent any voltage breakdown. The most power-demanding block of the system is typically the data TX 210. Therefore, the PMU 206 monitors the voltage level across $C_S$ and establishes active and sleep modes for the TX operation.

Figure 3A:
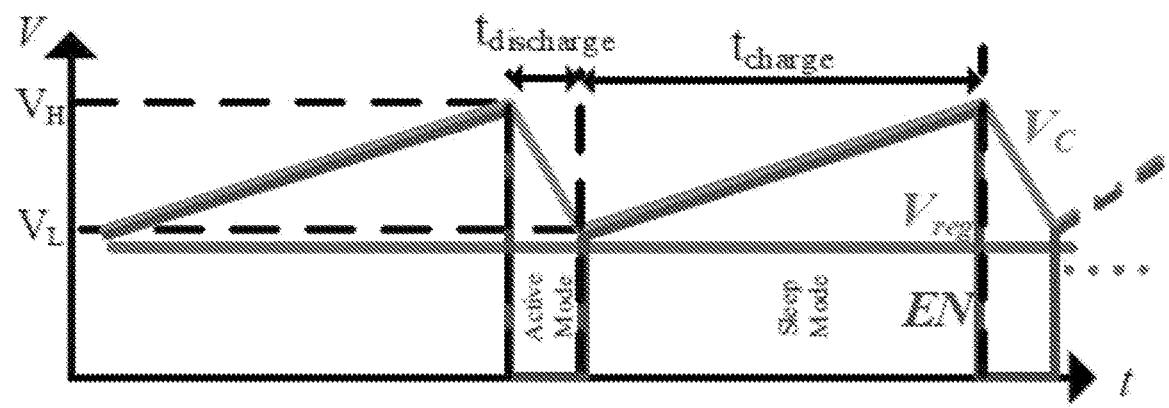
FIG. 3(a) graphically illustrates an example of duty-cycling power in a miniaturized neural implant in accordance with embodiments of the invention.

The maximum power that can be transferred to a mm-sized implant under safety regulations is reported to be in the order of hundreds of micro-Watts. On the other hand, the circuitry for implementing a data TX often demand a few milli-Watts of instantaneous power. A common technique to tackle this problem is duty-cycling the operation of power-demanding blocks. FIG. 1(b) illustrates the concept of duty-cycling in a miniaturized implant where power demanding blocks are deactivated frequently to allow power harvesting system to preserve a sustainable voltage for the rest of constituent blocks. The waveforms of the internal nodes of the PMU 206 in a duty-cycled power delivery scheme according to some embodiments are illustrated in FIG. 3(a). If the harvested power falls below TX power consumption, the TX block 210 can be periodically deactivated by the enable (EN) signal to allow the PMU to maintain $V_C$ higher than a minimum threshold amount ($V_L$) that is required for continuous operation of the RX block and internal circuitry of the PMU 206. For the entire duration of the sleep mode ($t_{charging}$), the rectifier charges the $C_S$ and $V_C$ rises until it reaches a predefined threshold ($V_H$).

Figure 3B:
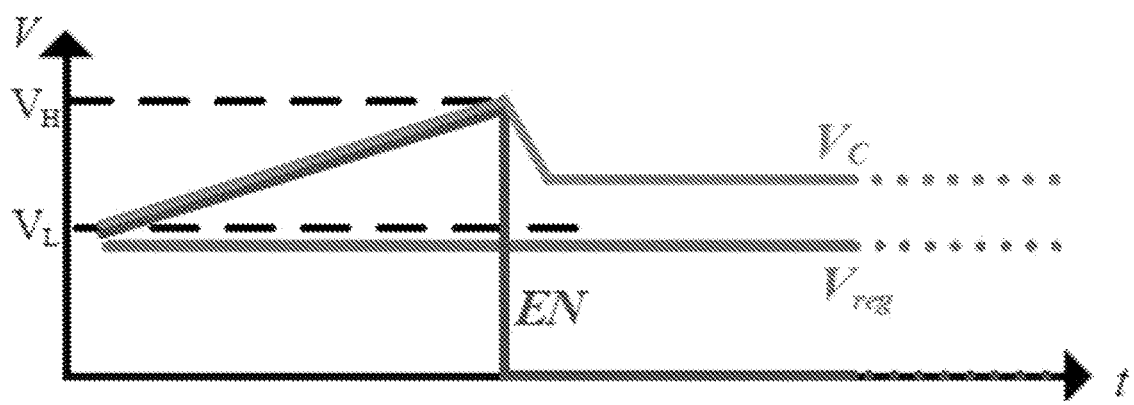
FIG. 3(b) graphically illustrates power being sufficient for a transmit block to remain active all the time in accordance with embodiments of the invention.

If the harvested power is sufficient for continuous operation, the TX block remains active all the time, EN stays low and $V_C$ settles at a voltage level between $V_H$ and $V_L$, as shown in FIG. 3(b).

Wireless Link Implementation

The wireless link of the transceiver system in accordance with several embodiments of the invention includes two distinct antennas that are used in DL and UL paths (the receive and transmit blocks). Mm-sized RF wireless power transfer (WPT) systems featuring an on-chip coil (OCC) as power receiver can have an operating frequency (receive) in the order of few tens or hundreds of MHz. High frequencies (e.g., higher than 10 GHz) cannot penetrate the body. To minimize the interference of the WPT system, the operating frequency of the data TX is extended to the GHz frequency region in several embodiments. Among various types of antennas, a dipole structure is an attractive choice for the UL path due to its simple profile and complicity with on-chip integration. The dipole antenna is also easy for on-chip implementation and has a small footprint. To enhance the harvested power for the system operation and maximize the data rate in the UL path, it is desirable to optimize the antenna dimensions and operating frequency.

Figure 4:
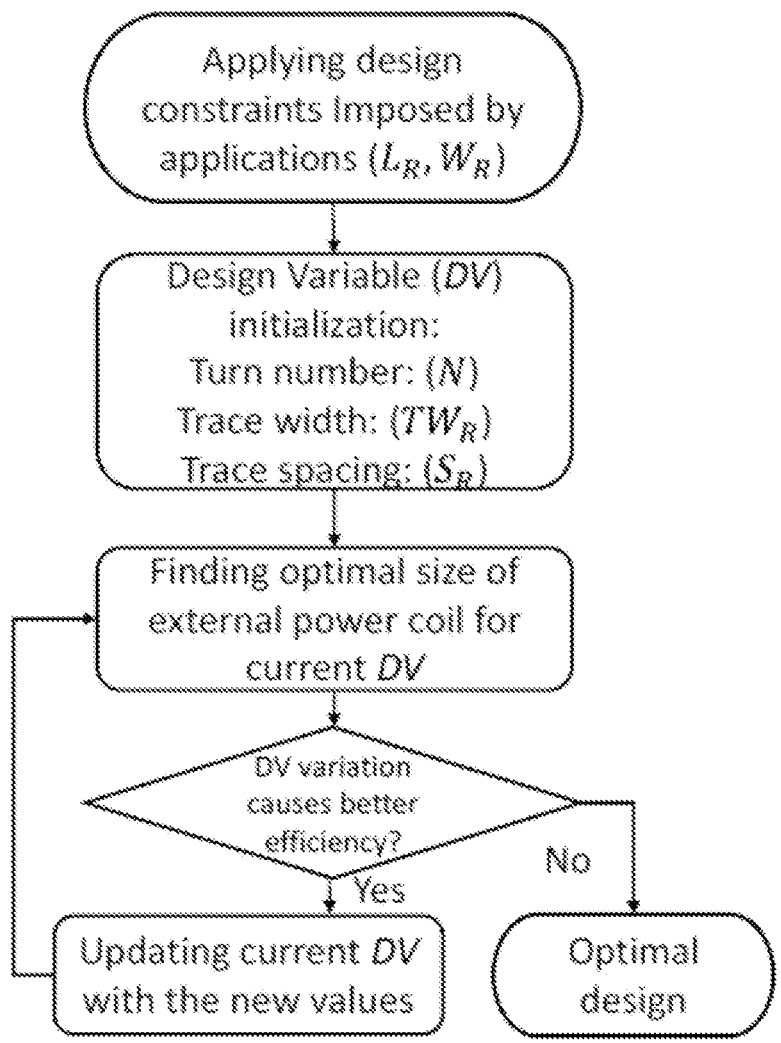
FIG. 4 illustrates a flow chart illustrating a process for the optimization algorithm for the power link.

For wireless power harvesting systems for small implants, link optimization, optimum operating frequency, the effect of intervening biological tissues, SAR limit, and rectifier design are of particular interest. The wireless link can be modeled as a two-port network and the link optimization can be conducted through an iterative algorithm that aims to maximize the power transfer efficiency. The two-port network model for a wireless link is a general approach and can be applied to any wireless link operating at near-field or far-field electromagnetic region with different link composition surrounding the antennas. Therefore, the a two-port network model can be applied for both DL and UL design of the transceiver. A flow chart illustrating a process for the optimization algorithm for the power link in accordance with some embodiments of the invention is shown in FIG. 4.

To recover larger amounts of power from the DL, it may be desirable to have a large signal. However, this can have undesirable effects on the transmitter. For example, at a frequency of 250 MHz, the harmonics also have power. The 17th harmonic of a power link at 250 MHz can interfere with the transmitter data signal. Therefore, a tunable capacitor may be utilized to change the resonance frequency of the receive antenna 212.

A calibration process may utilize power with an ideal supply voltage. The received spectrum of the UL can be measured with a spectrum analyzer. The power delivery link can be activated and the tunable capacitor can be tuned until the UL tone (data) is not affected in the presence of the power link.

Considering the mm-sized form factor, the maximum dimension of certain embodiments is limited to 2.25 mm and the distance between the external power transmitter and the OCC is set to 12 mm. Due to the relatively large coupling between the external coil and the OCC, the design variables of the OCC can be jointly optimized with the external power coil through an iterative optimization algorithm.

Figure 5:
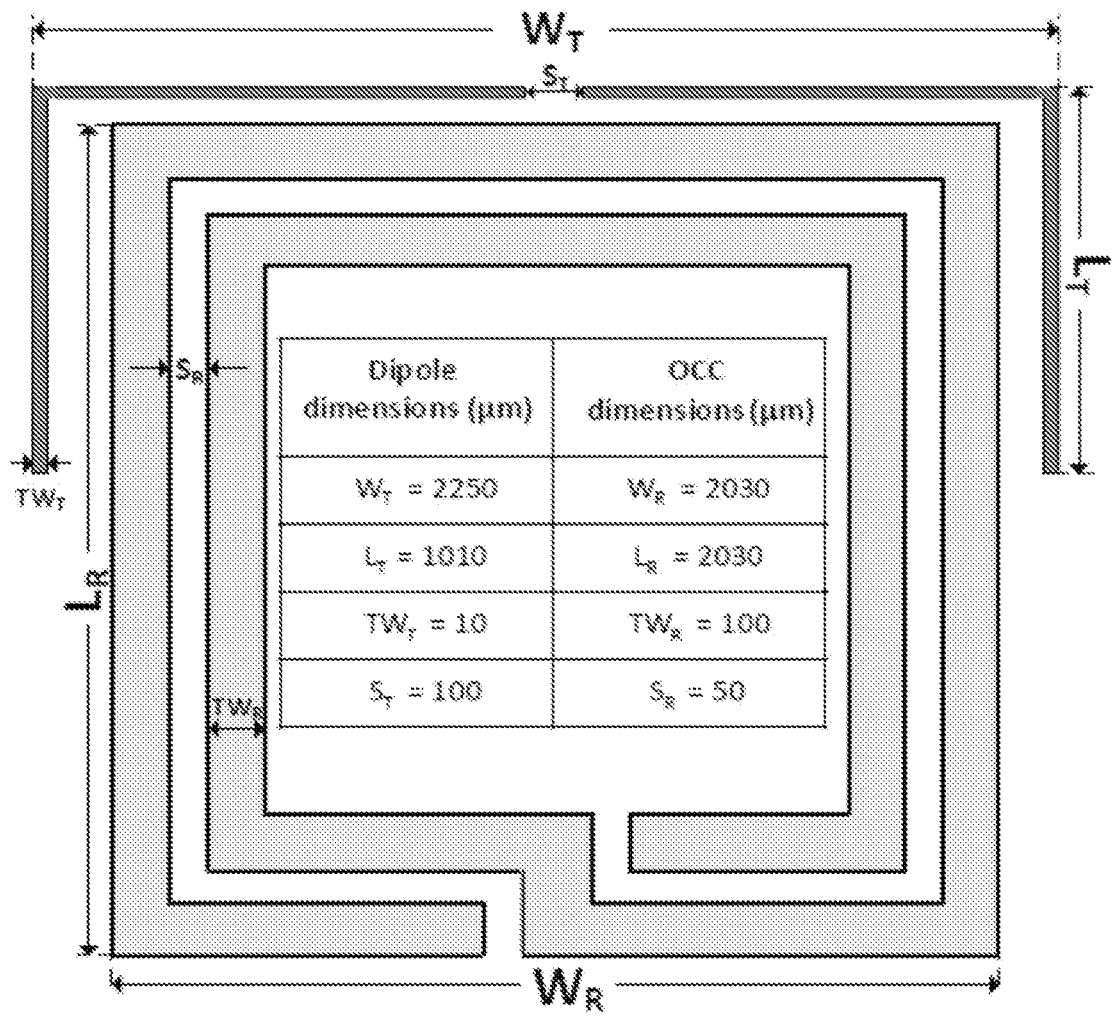
FIG. 5 illustrates optimal dimensions of the OCC and the dipole antenna according to several embodiments of the invention.

For UL communication, the transceiver in some embodiments utilizes an on-chip dipole that transmits TX data to an external UWB monopole antenna with a bandwidth of 3-7 GHz. The power transfer efficiency of the WPT system is susceptible to degradation by the presence of conductive material in the proximity of the power transmitter coil. To ensure that wireless power flow to the system is not altered by the UWB monopole antenna, the UL communication distance can be chosen to be 15 cm in some embodiments. The optimized design for the dipole antenna can be achieved using a similar optimization algorithm as the WPT system. However, due to the large distance and a weak coupling between the dipole and monopole antennas, the design variables of the monopole antennas may not change through the optimization process. The optimal dimensions of the OCC and the dipole antenna according to several embodiments of the invention are illustrated in FIG. 5. Simulation results show that the illustrated OCC has an inductance value of 13.6 nH and achieves an unloaded Q-factor of 14.3 at 250 MHz.

Power Management Unit

Figure 6:
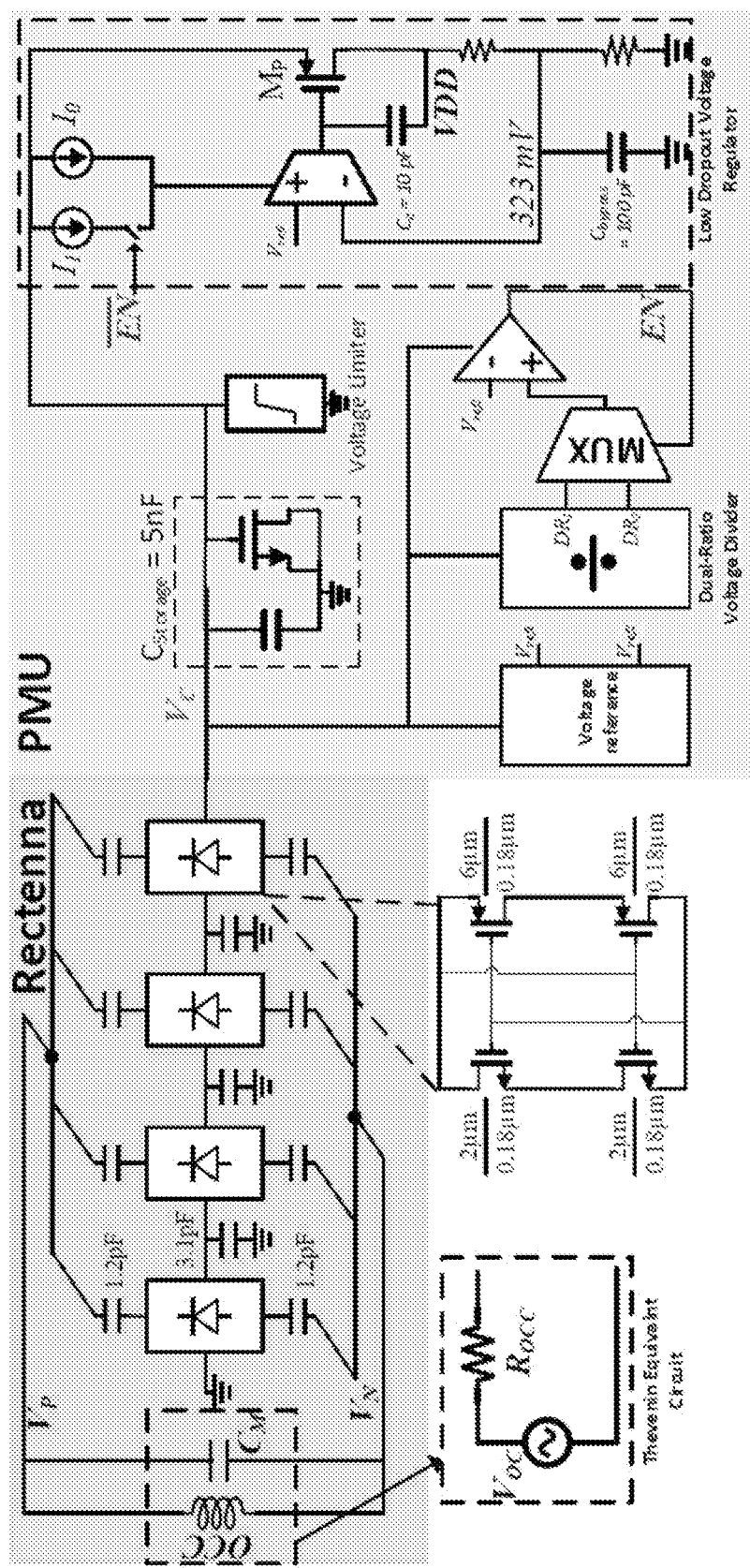
FIG. 6 illustrates a diagram of a power harvesting system in accordance with several embodiments of the invention.

A detailed diagram of a power harvesting system 202 in accordance with several embodiments of the invention is illustrated in FIG. 6. The rectenna is implemented with a four-stage full-wave rectifier to ensure $V_C$ reaches the required voltage level for the proper operation of the PMU 206 when the transmitted power of the external coil is kept below safety limits. Depending on the received power, and the Q-factor of the OCC, and the matching network, several architectures can be used for implementing a voltage rectifier, including, but not limited to, diode-connected MOS devices, native MOS, threshold-compensated, and self-driven rectifiers. Among various topologies, self-driven rectifiers with cross-coupled CMOS devices can provide a good balance between conversion efficiency and sensitivity. Hence, this configuration may be utilized for implementing a multi-stage voltage rectifier in some embodiments. To maximize rectifier RF-dc conversion efficiency, transistors dimensions are optimized. Moreover, deep N-Well NMOS transistors can be used to allow a direct connection between bulk and source terminals. Connecting bulk to source eliminates body effect and prevents increments of the threshold voltage of NMOS devices that ultimately improves RF-dc conversion efficiency. A first-order matching circuit can be realized using a shunt capacitor that resonates with the OCC and the voltage rectifier at the operating frequency. The shunt capacitor cancels out the imaginary part of impedance values. Hence, the power reflection between the OCC and the rectifier can be attributed to the difference in the real part of their impedances. An equivalent circuit model for the OCC is illustrated in FIG. 6 where the OCC is modeled as a source with an open circuit voltage of $V_{OC}$ and an internal resistance of $R_{OCC}$. At 250 MHz, EM simulation results show the $R_{OCC}$ as 305Ω. On the other hand, during the charging phase, the voltage rectifier periodically charges the storage capacitor from $V_L$ to $V_H$. Depending on the charging time, the load of the rectifier during the charging phase varies between 235 µW to 420 µW. For a 0 dBm of available power, the simulated conversion efficiency for an available power level of 0 dBm at 250 MHz varies between 30% 65%. Also, the Large Signal S-Parameter (LSSP) simulation of the rectifier indicates that the insertion loss between the OCC and the voltage rectifier is about 4.2 dB. Hence, the overall power transfer efficiency from the external coil to the rectifier is 24.2 dB. On the other hand, the sensitivity of the power harvesting system is defined as the minimum required power transmitted from the external coil to establish a hysteresis operation in the PMU. Based on the simulation results, the sensitivity of the power harvesting system is 21.5 dBm.

The behavior of the PMU 206 in the duty-cycled mode resembles a hysterics comparator that is realized using a voltage divider, a multi-level reference generator, a MUX, and a voltage comparator as shown in FIG. 6. The voltage reference block is realized with a supply independent proportional-to-absolute-temperature (PTAT) architecture to generate two reference voltages. Once the TX block is activated, $C_S$ discharges and $V_C$ drops rapidly. The $t_{discharge}$ is proportional to the value of $C_S$. Therefore, it is desired to maximize the capacitance value of $C_S$ to extend the active mode. To achieve the highest capacitance value with area constraints of an on-chip design, some embodiments have stacked MIM capacitors over MOSCAP devices with a density of 2f F/µm² and 5.5f F/µm², respectively to realize a 5 nF capacitor.

A low-dropout (LDO) voltage regulator can be incorporated into the PMU 206 to provide a constant 1.3 V dc voltage for the operation of the TX 210 and RX 208 blocks. During charging mode, the total current consumed by the LDO is 10 µA. The transition from sleep mode to the active mode represents a significant load variation for the LDO and a small quiescent current consumption of the LDO limits the transient response of the LDO. Hence, the abrupt variation of the load leads to a large voltage variation at the output of the LDO. The maximum instantaneous current drawn by the TX block 210 reaches as high as 4.5 mA which results in a maximum transient voltage variation of 175 mV. To ensure that the LDO remains functional in the active mode, the bandwidth of the error amplifier is increased at the onset of active mode. The PMU 206 can adaptively increase the bias current of the error amplifier by 100 µA which enables the LDO to maintain the voltage variation below 12 mV. It can ensure that the LDO stability conditions are met during the operation. Simulation results show that the minimum phase margin of the LDO is 88° and the gain margin always remains above 20.5 dB.

Although a specific implementation of a power management unit is discussed above with reference to FIG. 6, one skilled in the art will recognize that any of a variety of designs and characteristics may be utilized in accordance with embodiments of the invention as appropriate to a particular application.

Data Receiver Design

Figure 7:
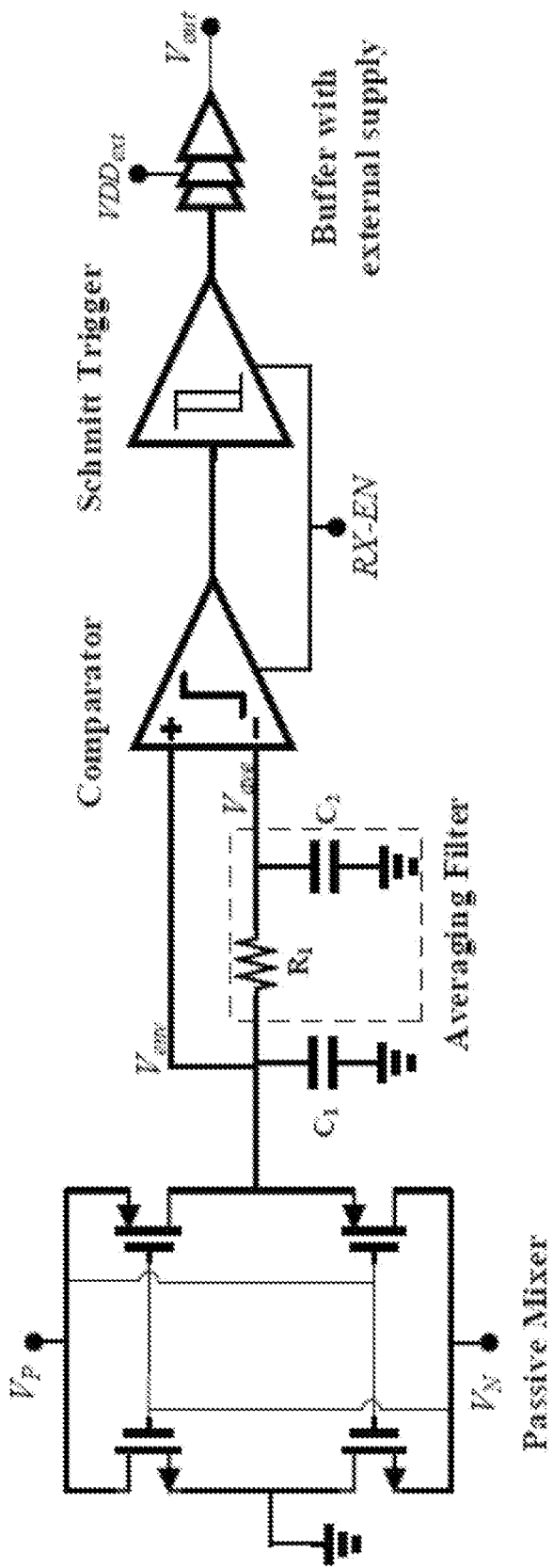
FIG. 7 illustrates a circuit schematic of receiver circuitry block and the corresponding waveforms in accordance with several embodiments of the invention.
Figure 8:
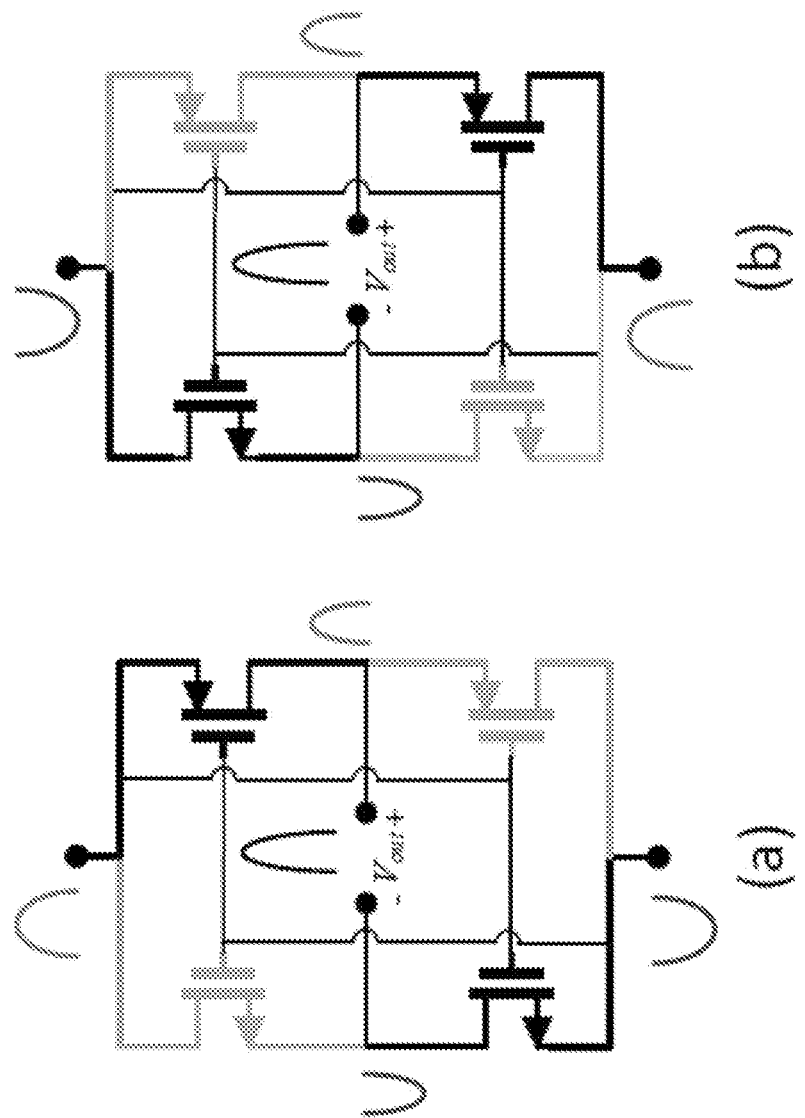
FIG. 8 illustrates switching status of transistors in positive and negative cycles in a receiver circuitry block in accordance with several embodiments of the invention.

A circuit schematic of the RX block 208 and the corresponding waveforms in accordance with several embodiments of the invention are shown in FIG. 7. The RX is based on a self-mixing architecture. In some embodiments, the power carrier is modulated with an ASK modulation scheme to carry the DL data stream. The received RF signal by the OCC can be formulated as in (1).

$$V_{RF} = V_P(t) - V_N(t) = A\cos(2\pi f_{RF}t)[1 + mx(t)] \qquad (1)$$

Where x(t) and m represent DL data and modulation index, respectively. Data modulation should have a minimal impact on power flow to the chip. Hence, the RX should be able to detect the DL signal with a very small modulation index. A passive mixer is implemented using the same circuitry as a single rectifier stage to minimize the power consumption of the RX. Inspecting the switching status of the transistors in positive and negative cycles of $V_{RF}$, shown in FIG. 8, reveals that a single rectifier stage can act as a self-mixer. The behavior of the self-mixer can be approximated as the multiplication of a square wave with a frequency of $f_{RF}$ with $V_{RF}$. Considering only the first harmonic of the square wave, the output of the mixer can be approximated as (2):

$$\begin{aligned} V_{out} &= V_{RF} \times \frac{4}{\pi} \sum_{n=1,3,5...}^{\infty} \cos(n \times 2\pi f_{RF}t) \\ &\approx V_{RF} \times \frac{4}{\pi}\cos(2\pi f_{RF}t) \\ &= \frac{2A}{\pi}[1 + mx(t)](1 + \cos(4\pi f_{RF}t)) \end{aligned} \qquad (2)$$

Figure 9:
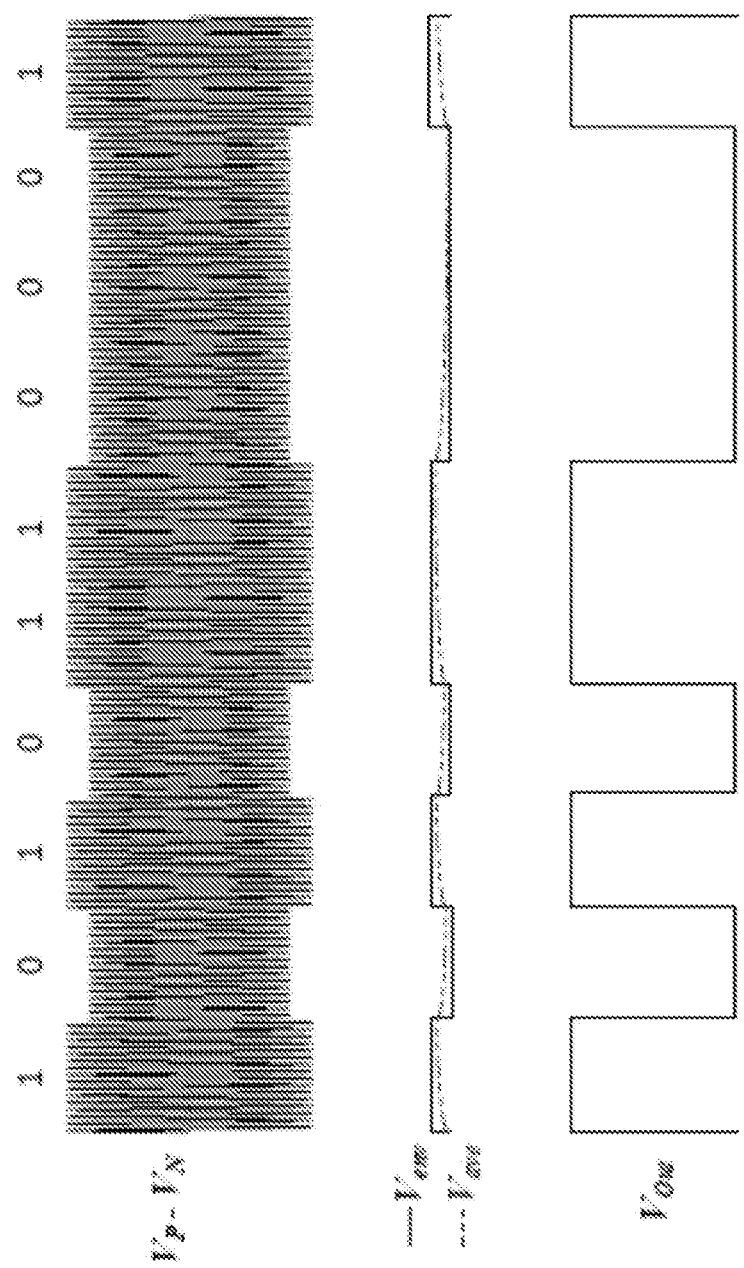
FIG. 9 illustrates a timing diagram in accordance with several embodiments of the invention.
Figure 10:
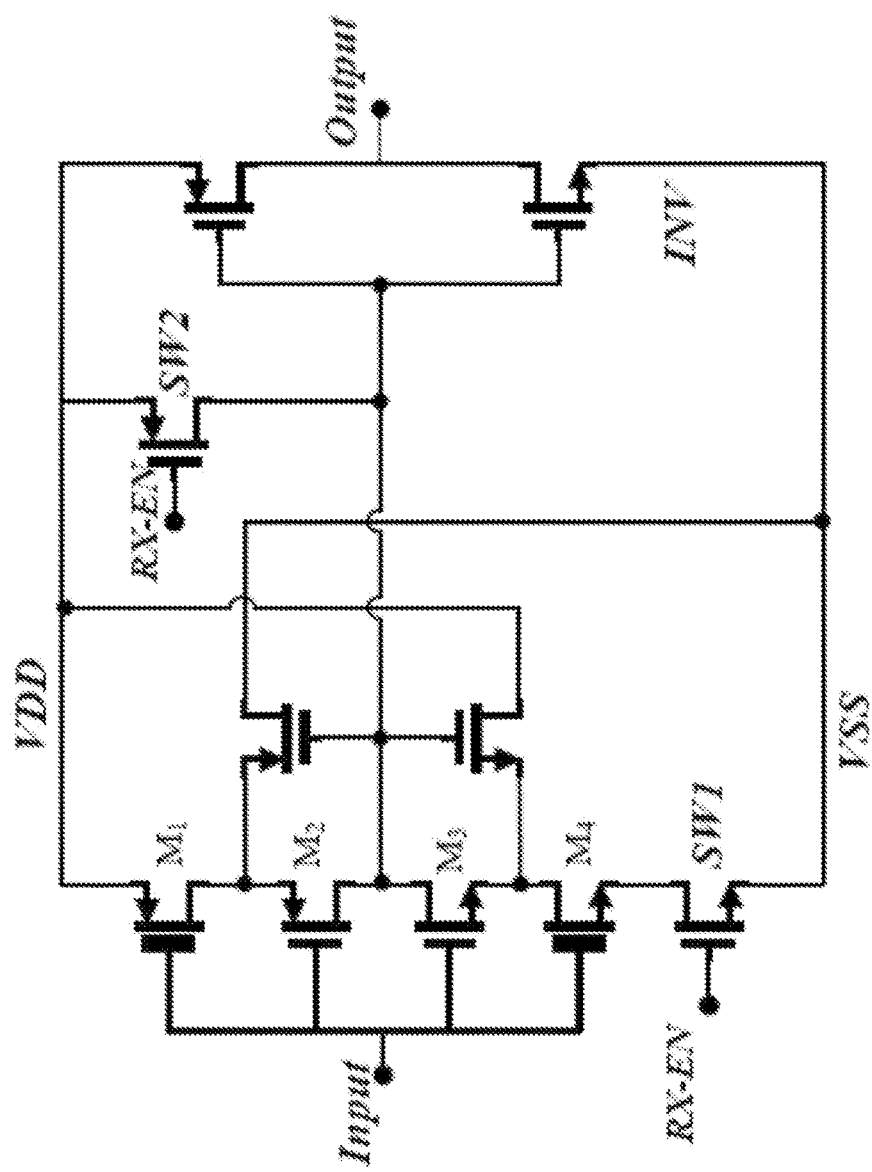
FIG. 10 illustrates a circuit schematic of a Schmitt trigger in accordance with several embodiments of the invention.

The required data rate for DL communication usually is a few Mbps. Hence, the frequency of x(t) is considerably lower than $f_{RF}$. In order to extract DL data, the output of the mixer can be passed from a band-pass filter (BPF) to remove frequency components at dc and $2f_{RF}$ whereabouts. It worth noting that the minimum required voltage amplitude for activating the voltage rectifier in the PMU is 650 mV. Hence, $V_{RF}$ can be directly passed to the mixer with no pre-amplification. Considering the frequency of the DL data, realizing a BPF with on-chip components is not realistic. Hence, in several embodiments, the BPF is implemented in three steps using low-pass filters (LPF) and a voltage comparator. The output node of the mixer in FIG. 7 is connected to a 10 pF shunt capacitor, which forms an LPF with the output resistance of the mixer. The LPF extracts the envelope of $V_{RF}$ that consists of a dc term and x(t), according to (1). Next, $V_{env}$ is passed through an LPF that has a cut-off frequency of 160 Hz. Due to the large time constant of the LPF, it acts as an averaging filter and the transition time of $V_{ave}$ is considerably larger than $V_{env}$. To remove the dc component and retrieve x(t), $V_{env}$ and $V_{ave}$ are passed to the voltage comparator. The simulated small-signal gain of the comparator is 51 dB with a 3-dB bandwidth of 3.8 MHz and current consumption of 280 nA. As evident in the timing diagram shown in FIG. 9, if x(t) does not toggle for multiple consecutive periods, $V_{ave}$ becomes closer to $V_{env}$. As a result, the comparator will be prone to meta-stability. To ensure that the fidelity of the recovered data is preserved, the comparator is followed by a Schmitt trigger that introduces a hysteresis effect. Hence, $V_{out}$ becomes insensitive to the voltage variation of the comparator in the meta-stable mode. The hysteresis effect also reduces the noise sensitivity of the RX block. The circuit schematic of the Schmitt trigger in accordance with several embodiments is demonstrated in FIG. 10. Transistors are sized properly to achieve a hysteresis window from 385 mV to 935 mV. The output of the Schmitt trimmer is passed to an on-chip buffer that is powered with an external supply in order to enable a direct connection to a voltage oscilloscope for measurement purposes.

Although a specific receiver circuitry is described above with respect to FIG. 7, one skilled in the art would recognize that variations may be made or other circuitry may be utilized in accordance with embodiments of the invention as appropriate to a particular application.

Data Transmitter Design

In many embodiments of the invention, the TX block is realized with minimal complexity to reduce overall power consumption. Thanks to the amplitude-based modulation, there is no need for generating an accurate frequency. Therefore, process, voltage, and technology variation can be tolerated which significantly relaxes the constraints on the TX circuit design. As a result, a free-running oscillator is adequate to generate a GHz-range carrier frequency for the TX. Data transmitters based on amplitude modulations may utilize an LC oscillator is followed by a power amplifier to drive the antenna. However, the total power consumption of such transmitters is above 10 mW which limits the data rate and energy efficiency. To reduce the power consumption of the TX, the transceiver system can utilize a Power Oscillator (PO) as the core of the TX block in several embodiments of the invention. The PO may be directly connected to the dipole antenna and drives it without the need for any extra power consumption in buffers. Hence, many embodiments utilize a co-design approach for the PO and the dipole antenna to set the resonance frequency and maximize the dc-RF efficiency of the TX. At the resonance frequency, the antenna can be modeled by a parallel resistor ($R_{P,a}$) and a shunt capacitor ($C_{P,a}$). An equivalent model for the PO is demonstrated alongside its circuit schematic in FIG. 11. The PO is realized with a class-D topology where the tail transistor is removed which results in the elimination of the overhead voltage. Unlike conventional oscillators, transistors in class-D operate as close-to-ideal switches and thus $M_1$-$M_4$ are sized properly to guarantee a small on-resistance. Because of the high oscillation amplitude, this structure is popular for low-phase-noise and low-power applications. The product of current through MOS switches and the supply voltage is negligible across the oscillation period and the class-D achieves an energy efficiency of 90%. The power consumption of the PO is dominantly determined by the parasitic resistance of the tank inductor. Operating at high frequencies and using a large tank inductor with a better Q-factor is desirable to minimize the power consumption of the PO. However, wireless link simulation results indicate that the UL efficiency is degraded rapidly at frequencies higher than 5 GHz. Thus, the PO is designed for a center frequency of 4.2 GHz. To guarantee the oscillation happening in the PO, the effective transconductance of the complementary switches should overcome the losses of the inductor and the dipole antenna. The startup condition of the oscillator can be expressed in (3):

$$G_M > \frac{1}{R_P} + \frac{1}{R_{P,a}} \quad (3)$$

Figure 11:
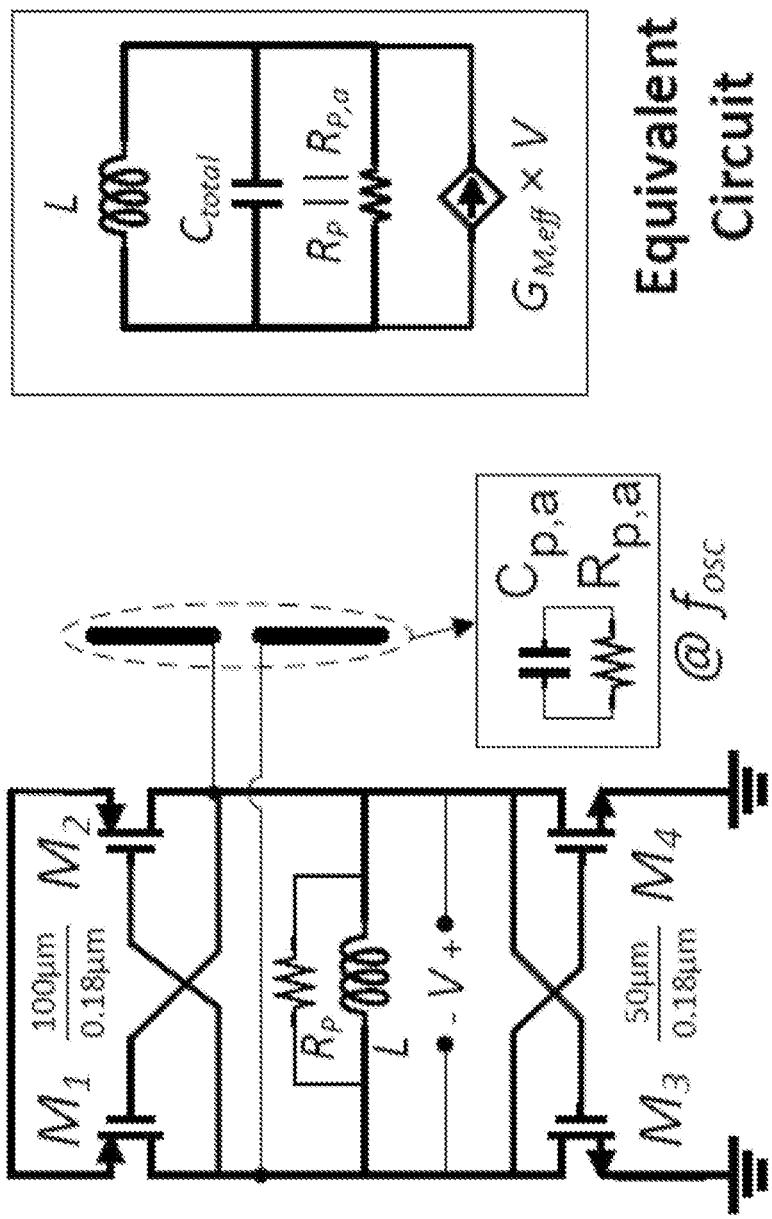
FIG. 11 illustrates an equivalent model for a power oscillator (PO) in accordance with several embodiments of the invention.

To maximize the effective transconductance during the oscillation period ($G_M$), a complementary cross-coupled pair can be utilized to boost the $G_M$ through a current reusing technique. Also, transistor $M_1$ $M_4$ are properly sized to ensure the oscillation conditions are met across all technology corners. Although switching performance and $G_M$ of $M_1$ $M_4$ improves as they become larger, the parasitic capacitance associated with them also increases with size and reduces the PO resonance frequency. Hence, in certain embodiments the transistors are sized as shown in FIG. 11.

The impact of surrounding tissues on the PO can be evaluated by careful EM simulation of the dipole antenna and the tank inductor in IE3D. Using the same EM configuration for the chip as before, the S-parameters are extracted and used in circuit simulation of the PO. Table I reports the resonance frequency of the PO across various types of biological tissues in its vicinity. Also, the impedance of the dipole antenna at the resonance frequency and the ratio of delivered power to the antenna over the total power consumption of PO ($\eta_{DC-RF}$) are included in the Table. The oscillator is simulated with a 1.3-V supply voltage assuming all components are in the typical technology corner. The simulation results suggest a negligible frequency shift.

TABLE I

THE IMPACT OF SURROUNDING MEDIUM ON THE DIPOLE ANTENNA IMPEDANCE AND THE PO OPERATION

| Medium | Freq. (MHz) | $Z_a$ ($\Omega$) | $\eta_{DC-RF}$ (%) |
|---|---|---|---|
| Air | 4224 | 74.15 − j243.47 | 35 |
| Fat | 4207 | 66.29 − j241.96 | 33.8 |
| Muscle | 4198 | 63.17 − j240.12 | 33.4 |
| Skin | 4193 | 61.80 − j239.05 | 33.3 |
| Skull | 4199 | 63.41 − j240.35 | 33.4 |

One of the advantages of implementing the TRX with an FDD scheme is the minimal impact of the power link on the TX operation. To verify this assumption, a simulation can show the coupling efficiency between the external power transmitter and the dipole antenna connected to the tank inductor. Assuming a power carrier of 250 MHz, the seventeenth harmonic of the power carrier (4250 MHz) is the closest harmonic to the free-running frequency of the PO. The undesired coupling efficiency between the power carrier and the PO is 63.4 dB, 83.7 dB at 250 MHz and 4250 MHz, respectively. Due to the large isolation, the power link does not affect the PO operation and no frequency deviation from the free-running frequency is observed in the TX block.

Figure 12:
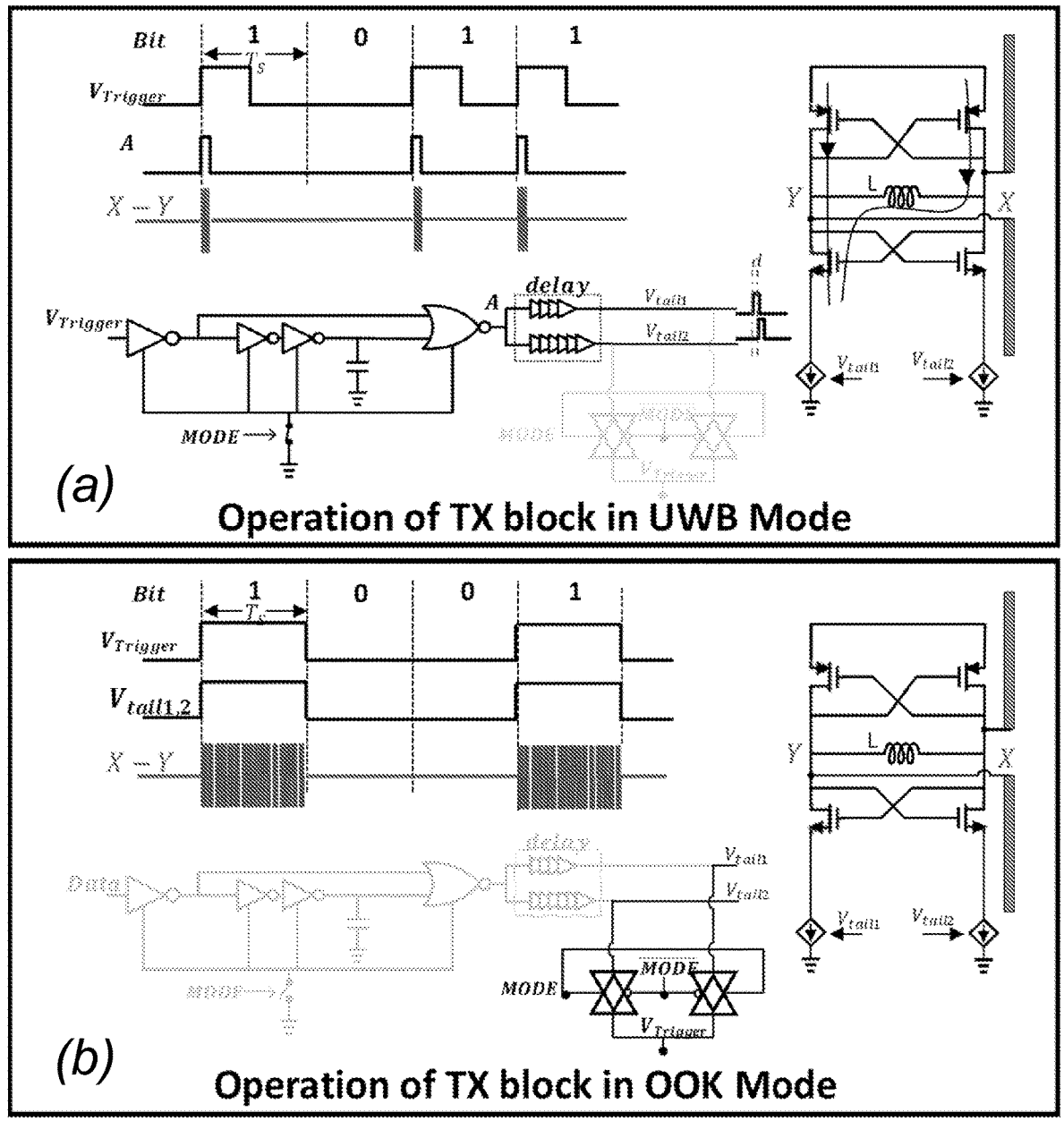
FIG. 12 illustrates a circuit schematic of the reconfigurable TX and the corresponding waveforms in operating modes in accordance with several embodiments of the invention.

In various embodiments, the TX block can be configured to conduct UL communication with either OOK or UWB modulation scheme. The circuit schematic of the reconfigurable TX and the corresponding waveforms in both operating modes are depicted in FIG. 12. The trigger signal for enabling the PO is shaped and fed to the TX block according to the modulation type. When operating in OOK mode, the trigger signal replicates the data pattern whereas, in UWB mode, it is shaped as a Return-to-Zero (RZ) waveform for symbol "1" as shown in FIG. 12(a). The operating mode of the TX can be controlled by an external mode selection signal that alters the signal path from the trigger to the PO. In OOK mode, the trigger signal is passed to the PO through a pair of transmission gates to control two switches that connect the NMOS cross-coupled pair to the ground. The switches are realized with NMOS transistors and are sized x8 larger than the NMOS cross-coupled pair. As depicted in FIG. 12(b), during transmission of a "1" symbol, the PO is active for the entire symbol period ($T_S$), which results in smooth switching transitions. Consequently, the transmitted signal from the PO occupies less bandwidth and can be detected with a simpler receiver. However, the average power consumption of the TX block in OOK mode is independent of the data rate and is merely determined by the instantaneous power consumption of the PO. The continuous power received by the power harvesting system is about a few hundreds of micro-Watt. On the other hand, the power consumption of the TX block is in the milli-Watt range and it is expected that the data communication in the OOK mode to be duty-cycled. The TX block can achieve a significantly lower average power consumption in UWB mode at the expense of a larger occupied bandwidth. In UWB mode, the trigger signal is first passed through a digital circuitry that generates a short impulse ($T_M \approx 2$ ns) upon the detection of a rising edge in the trigger waveform. Due to the small impulse duration, it is important to ensure that the PO can reliably startup. Asymmetric driving of an oscillator can achieve a fast startup. Therefore, generated impulse is delayed by inverter chain delay lines that connect SW2 slightly after SW1. The current flow during the startup time window through the PO, shown with arrow lines in FIG. 12(b), creates an initial voltage difference across node X and Y that results in a startup time of ~200 ps.

In further embodiments of the invention, the location of a wireless powered transceiver can be determined. For example, a reader device can receive the transceivers transmitted signal. The frequency and phase of the transmitted signal can be used to determine the distance between the transceiver and the reader device. Multiple distances can be determined by moving the reader device or by using multiple antennas on the reader device. A location can be determined for the transceiver using the multiple determined distances.

Although a specific transmitter circuitry is described above with respect to FIGS. 11 and 12, one skilled in the art would recognize that variations may be made (e.g., using other appropriate frequencies and/or modulation schemes) or other circuitry may be utilized in accordance with embodiments of the invention as appropriate to a particular application.

Measurement Results

In several embodiments of the invention, a circuit design as described above is fabricated in 180 nm CMOS technology. To evaluate performance, the chip is mounted on a Printed Circuit Board (PCB) and connected to PCB traces with bond wires. A non-conductive epoxy is poured on the chip and bond wires to protect the connections when a layer of tissue is placed on top of the chip. First, the dc response of the PMU is measured by connecting the $V_C$ node to a supply voltage and increase it gradually. The measured response of the PMU shows the hysteresis behavior of the PMU. Threshold values of the hysteresis loop are 1.5 V and 2.3 V and the output of LDO is measured as 1.34 V.

Figure 13:
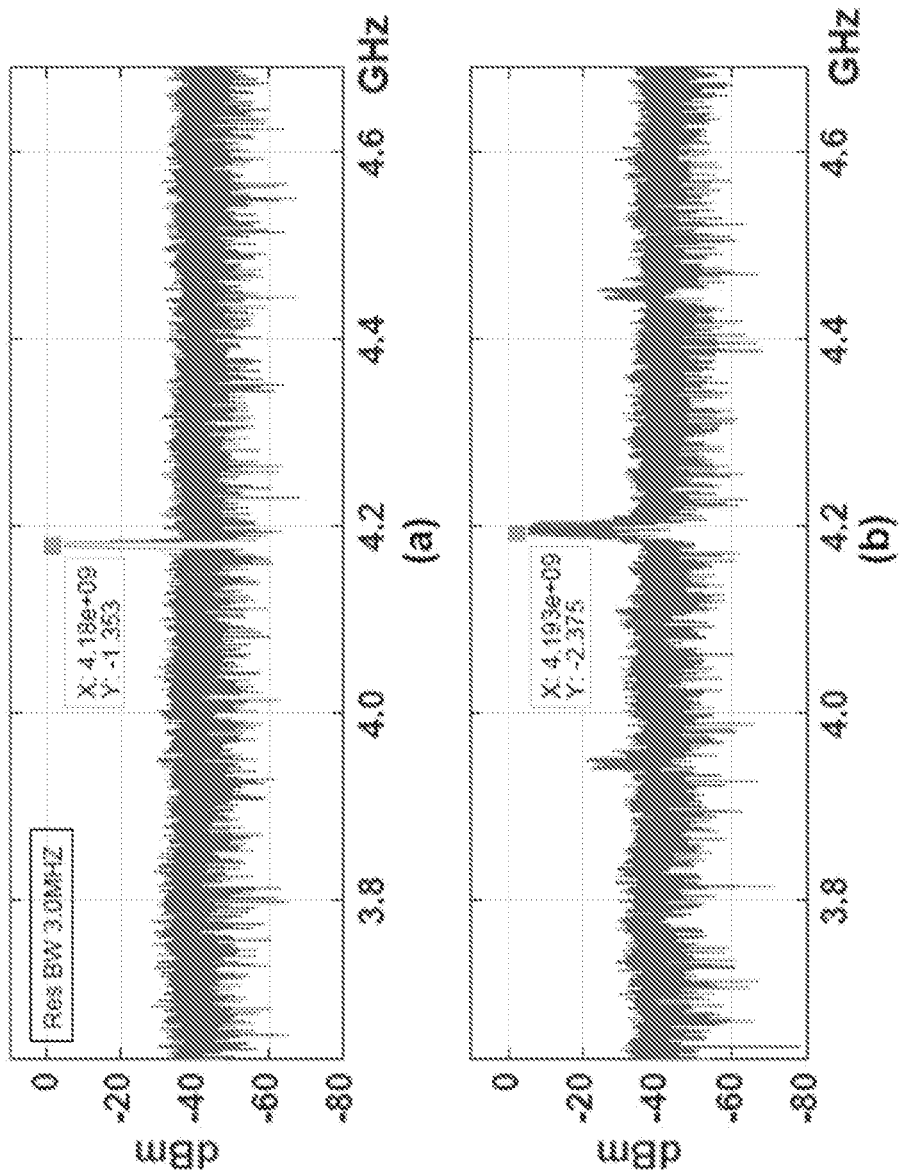
FIG. 13 illustrates spectrum of the radiated signal from the TX block in absence of a power carrier in accordance with several embodiments of the invention.

In WPT systems for medical implants, the transmitted power from the external coil ($P_{TX}$) is determined by the SAR limit. For frequency ranges below 500 MHz, the maximum SAR value is less than 1.6 W/kg when PT X≤30 dBm. The $P_{TX}$ may be increased even more at 250 MHz. However, PO operation is disturbed in presence of a strong power carrier through the injection pulling phenomena. Although injection pulling of the PO is not expected based on the simulation results that indicate high isolation between the DL and UL paths, the bond wires, and PCB traces. The use of PCB traces and bond wires is important during the measurement process to feed the UL data pattern to the chip. To determine the maximum $P_{TX}$ level before PO pulling, the system is powered with a dc supply and the $P_{TX}$ level is increased gradually. FIG. 13 shows the spectrum of the radiated signal from the TX block in absence of a power carrier. When the Pix reaches 26 dBm, additional frequency tones are observed in the TX spectrum and the free-running frequency is slightly pulled. The injection locking in the PO is problematic because of the creation of undesired side tones and also the attenuation of the main frequency tone.

The $P_{TX}$ threshold was measured for other frequencies as well and a similar behavior was observed. Hence, during the rest of the measurement, the $P_{TX}$ level was limited to 25 dBm and the modulation index of the DL communication set to 20% to ensure the instantaneous power level is below the injection pulling threshold.

Figure 14:
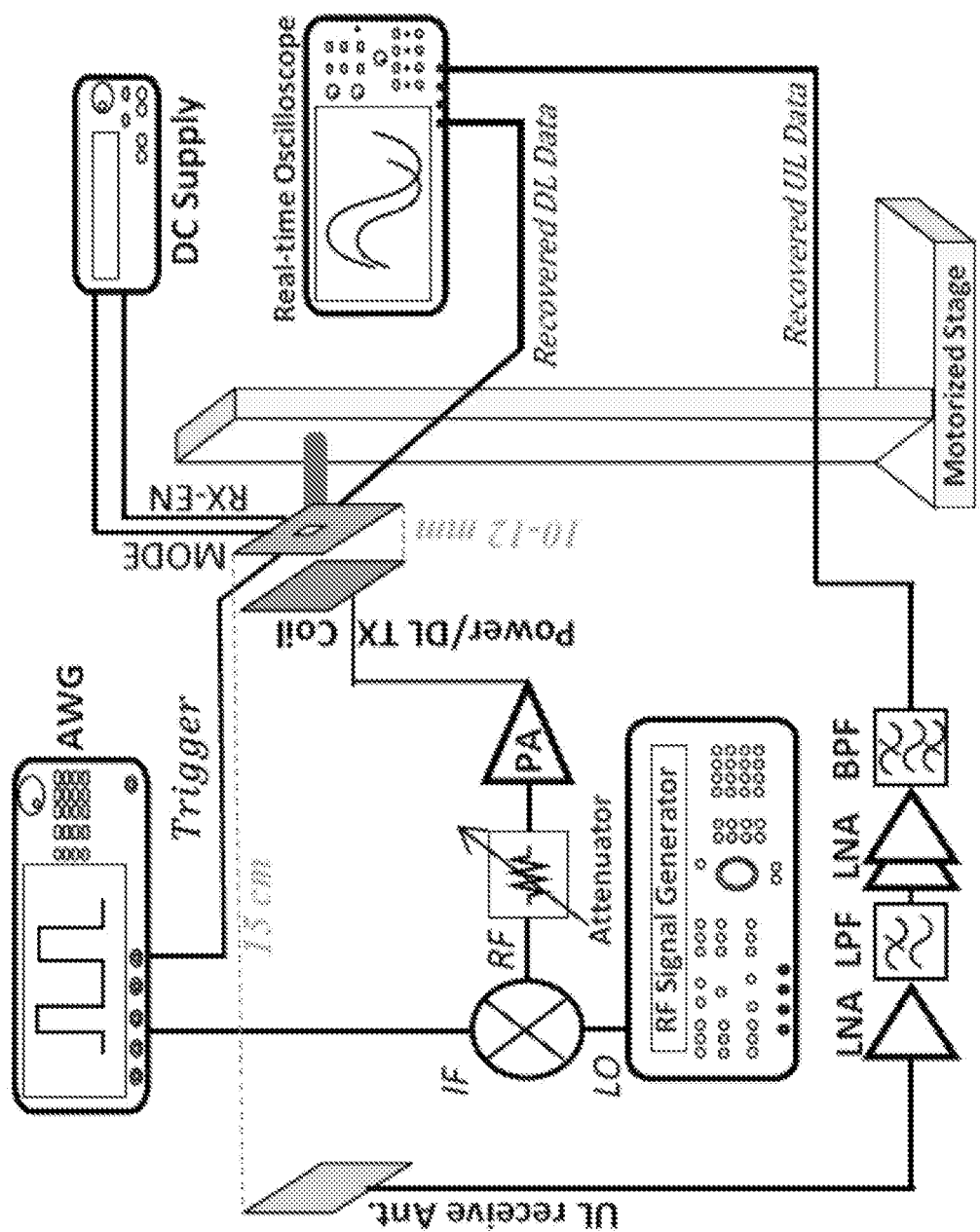
FIG. 14 illustrates a measurement setup for wireless characterization of a transceiver system in accordance with several embodiments.

A measurement setup for wireless characterization of a transceiver system in accordance with several embodiments is shown in FIG. 14. The power carrier is mixed with the DL data stream using a coaxial frequency mixer (e.g., Mini-Circuits ZX05-1LHW+) and is radiated towards the chip with a custom-built loop antenna that is matched to a 50-Ω source. The modulation index is controlled by adjusting the high-level and low-level of the IF port of the mixer. The RF port of the mixer is passed through an attenuator to ensure the input power level to the following power amplifier (PA) remains lower than the maximum ratings of the PA. A 1-cm thick chicken breast was used to evaluate the impact of an intervening biological tissue in the wireless link.

Figure 15:
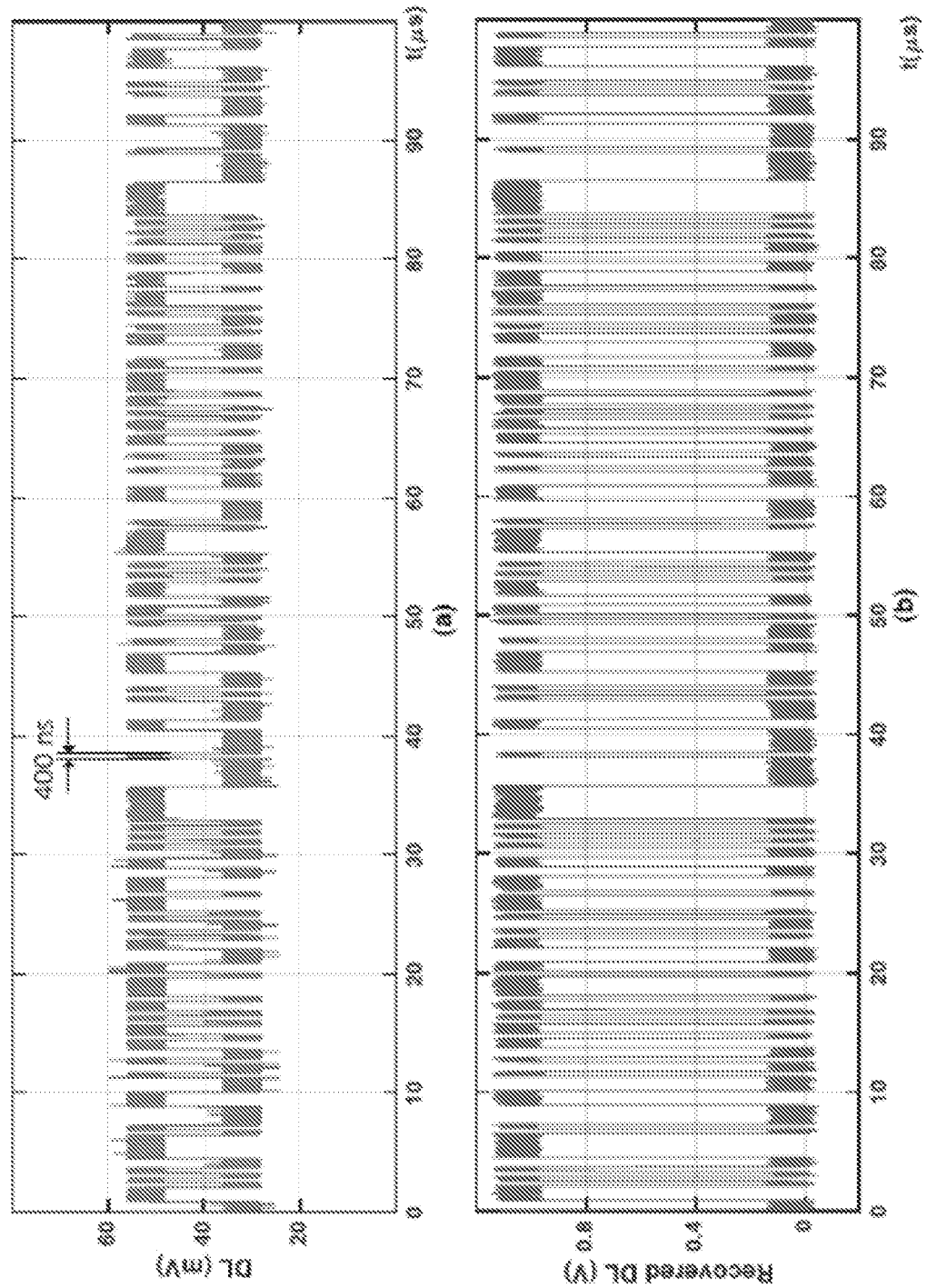
FIG. 15 illustrates recovered DL data alongside the original DL data stream in accordance with several embodiments.
Figure 16:
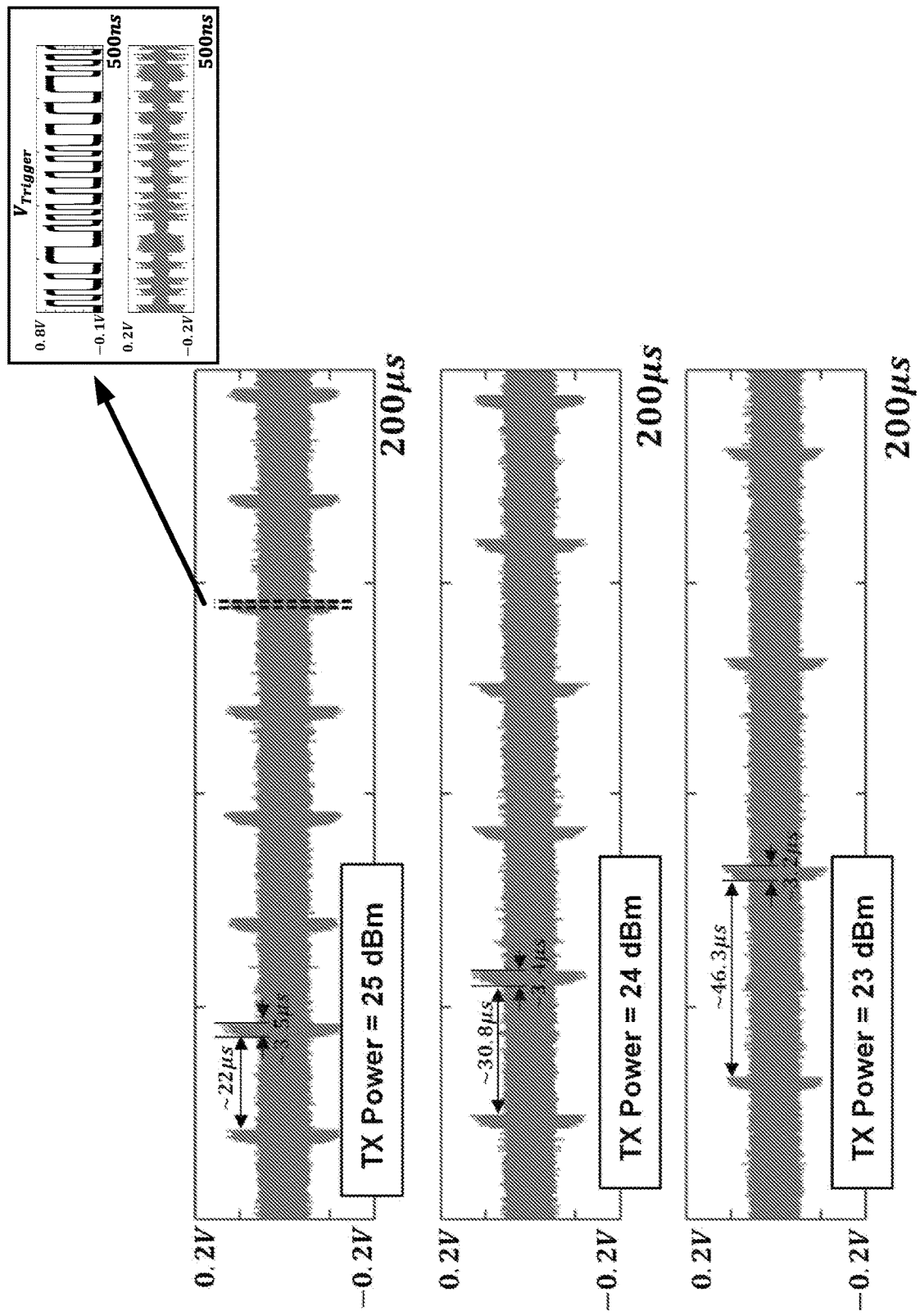
FIG. 16 illustrates recovered UL data in accordance with several embodiments of the invention.
Figure 17:
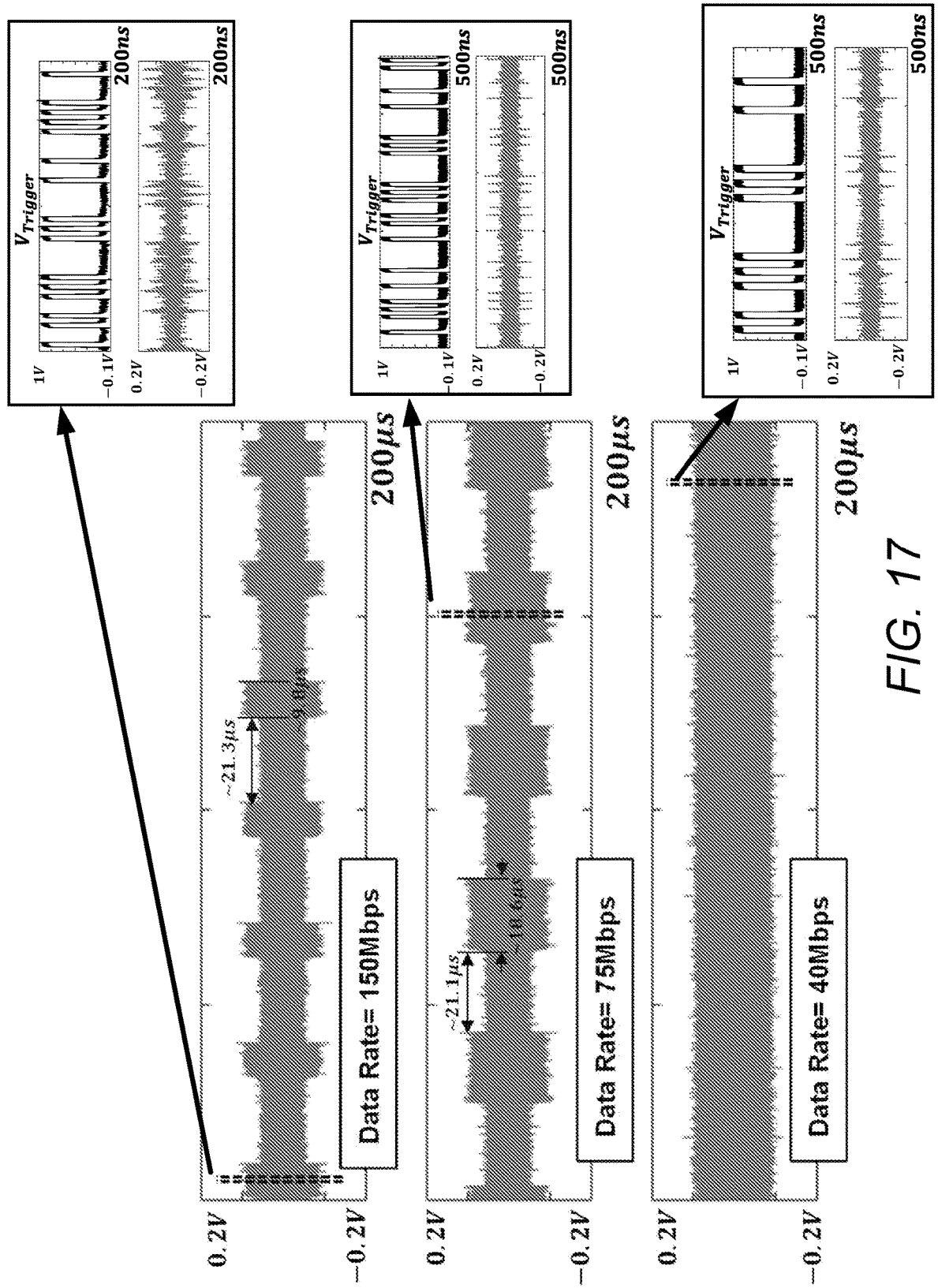
FIG. 17 illustrates performance of the radio measured in UWB scheme with various data rates and the recovered UL data in accordance with several embodiments of the invention.

First, the transceiver system is measured in the absence of chicken breast in the link and the power coil and the chip are separated with a 10 mm air gap. A wideband monopole antenna with the gain of 3.6 dBi (e.g., CHICOLAS ANT110) is placed 15 cm away from the chip to receive the UL data. After setting the $P_{TX}$ and the modulation index to 20%, the TX is configured in OOK mode and the recovered UL and DL data streams are recorded by real-time voltage oscilloscopes. FIG. 15 shows the recovered DL data alongside the original DL data stream with a data rate of 2.5 Mbps. It is evident that the recovered DL data follows the randomly generated data pattern by the arbitrary wave generator (AWG). Similarly, the random UL data pattern from the AWG and the received data by the monopole antenna are recorded and compared with a real-time voltage oscilloscope to verify the performance of the TX communication. To drive the 50-Ω impedance of the voltage oscilloscope, the monopole antenna is followed by additional gain stages and the detection bandwidth is limited by external filters. The ability of the PMU on adjusting the duty-cycle of UL communication is tested by sweeping the $P_{TX}$ from 23 dBm to 25 dBm. The TX is configured in the OOK modes and the data rate is set to 100 Mbps. The recovered UL data is measured with different $P_{TX}$ levels and shown in FIG. 16. The discharging time is almost constant in all three cases whereas the charging time increases as the Pix level drops. This observation is expected considering the PMU decreases the duty-cycle of UL communication to lower the average power consumption of the system. Similar behavior was observed when the TX was configured in the UWB mode and the $P_{TX}$ was swept. Unlike the OOK scheme, the power consumption of the TX is dependent on the data rate in the UWB mode as described before. The performance of the radio is measured in UWB scheme with various data rates and the recovered UL data is shown in FIG. 17. During this test, $P_{TX}$ is set to 25 dBm and the data rate is decreased from 150 Mbps to 40 Mbps. By inspecting the recovered UL data, it is evident that the duty-cycle of UL communication increases at lower data rates. Interestingly, for data rates below 40 Mbps, the proposed radio achieves a continuous UL communication.

Figure 18:
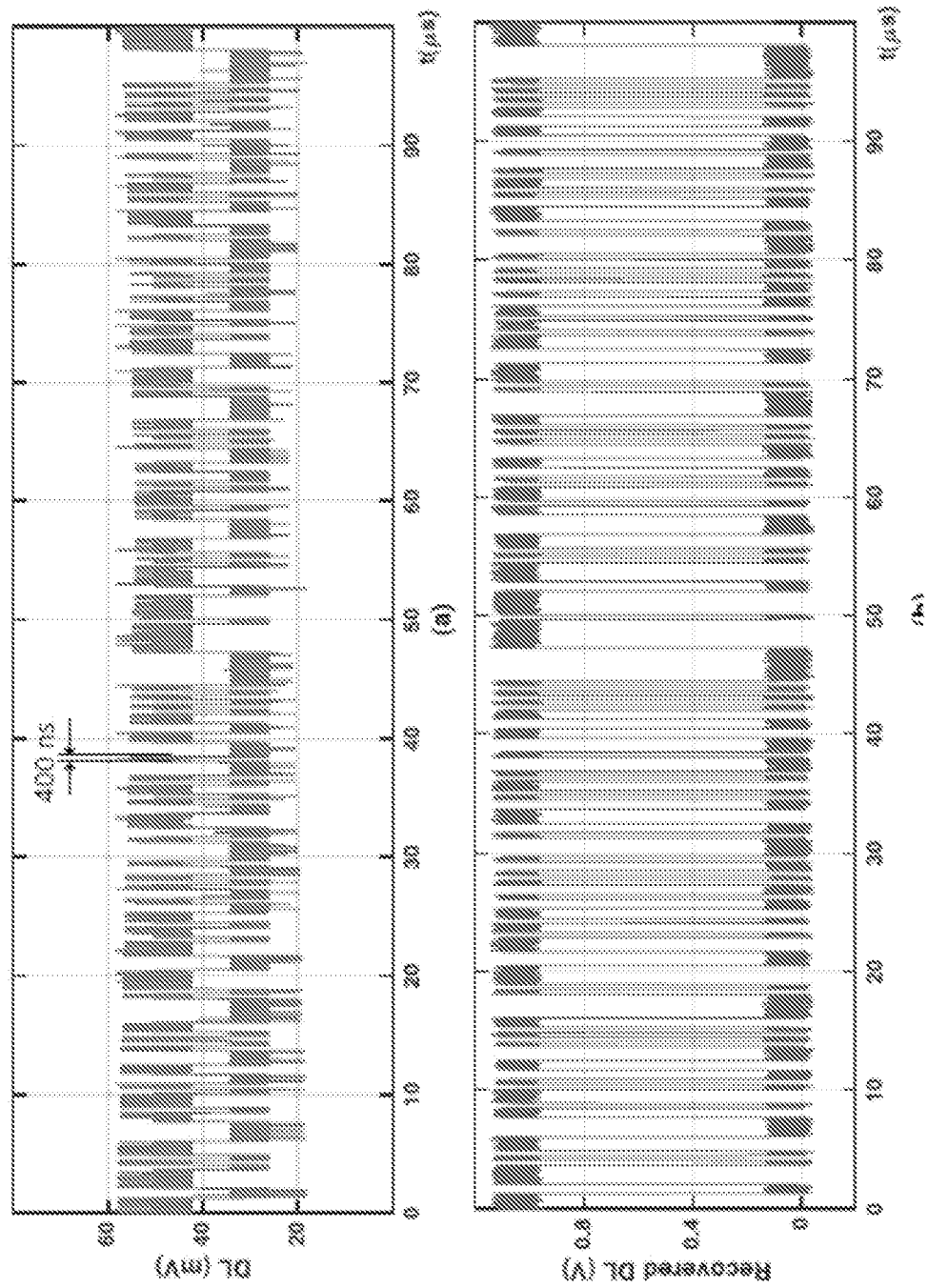
FIG. 18 illustrates recovered DL data is recorded with the oscilloscope and compared with the original DL data stream in accordance with several embodiments of the invention.
Figure 19:
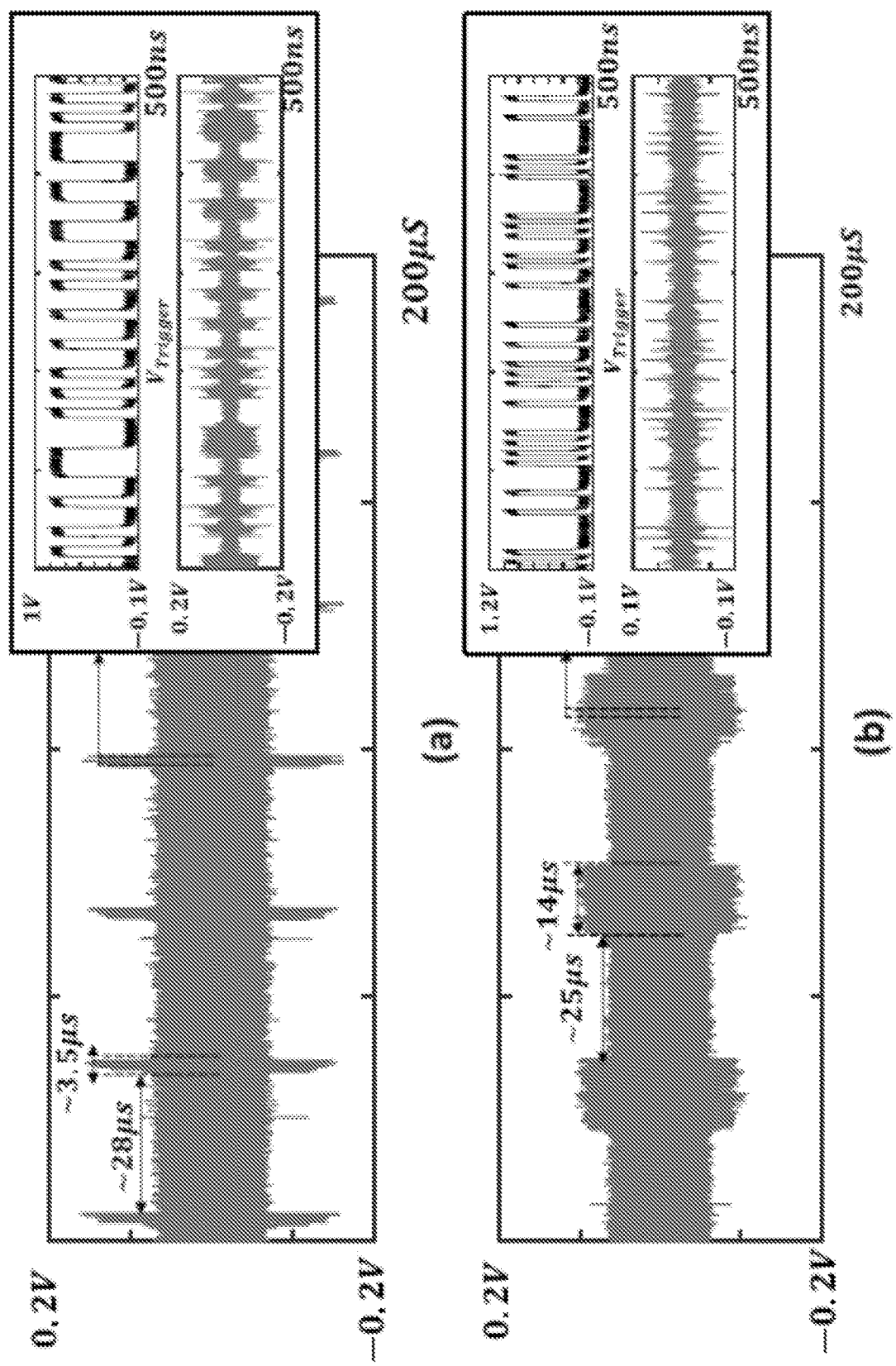
FIG. 19 illustrates measurement results for both OOK and UWB modulation schemes in accordance with several embodiments of the invention.

Next, the performance of the TRX is evaluated while the chip was covered with a layer of chicken breast with a thickness of 10 mm. The external power coil was placed 2 mm away from the chicken breast. Through an iterative search, the optimum frequency for power transmission was determined as 212 MHz. The external power coil was matched to the 50-Ω impedance of the source using mechanical trimmer capacitors. Also, a trimmer shunt capacitor was used to set the resonance frequency of the OCC to 212 MHz as well. After putting the TX in OOK mode, the chip was wirelessly powered with a $P_{TX}$ level of 25 dBm and the modulation index was set to 20%. The recovered DL data is recorded with the oscilloscope and compared with the original DL data stream. FIG. 18 shows that similar to the wireless test with no tissue, the RX can successfully receive the DL with a data rate of 2.5 MBps. Last, the UL communication is evaluated in presence of the chicken breast in the DL wireless path. Measurement results for both OOK and UWB modulation schemes are shown in FIG. 19 where the TX block supports OOK and UWB modulation schemes with a data rate of up to 100 Mbps.

To calculate the Bit-Error-Rate (BER) of the communication links, the time-domain waveforms were recorded multiple times and the recorded data processed with MATLAB offline. For each case, enough data was recorded to compare 10,000 recovered bits with the original data. After offline processing, no missing bit was observed. Hence, the BER of DL and UL communication is below 10'.

Figure 20:
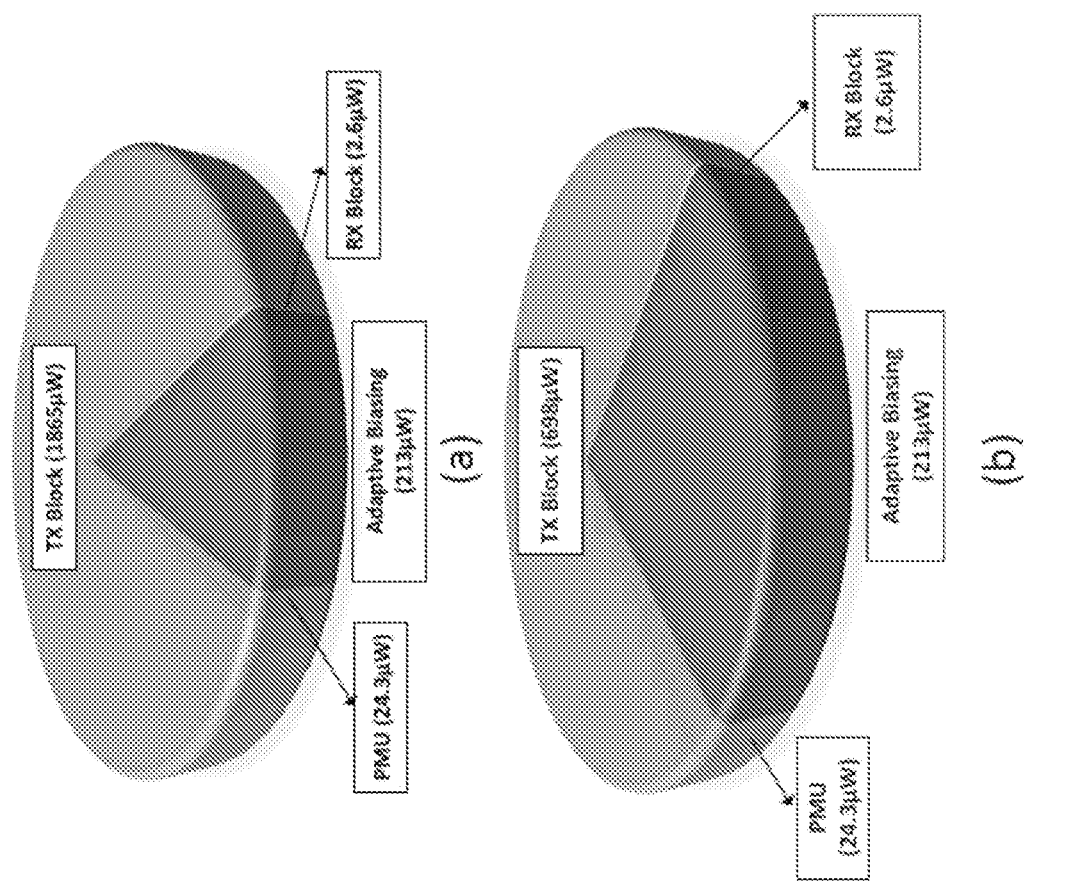
FIG. 20 shows power contribution of the building clocks in both OOK and UWB modulation schemes in accordance with several embodiments of the invention.

Finally, the power contribution of individual blocks is measured through a dc test. The measured power consumption of the PO is 3.73 mW. When the PO is used for data communication, the overall power consumption of the TX block is scaled according to the modulation scheme. The power contribution of the building clocks in both OOK and UWB modulation schemes are reported in FIG. 20. As expected, the power consumption is dominated by the TX block in both operating modes. Since the TX block is fed with a random data sequence with an equal probability of "0" and "1" bits, the TX power consumption in OOK mode is almost half of the power consumption of PO. The peak transmitted power of the TX can also be estimated with the aid of simulation results that indicates the $\eta_{DC-RF}$ efficiency of the PO as 35%. Hence, based on the power gain simulation results, at a 15 cm distance through the air, it is expected to receive the UL data with a peak power of 60 dBm. Excluding the additional gain of the components following the monopole antenna, the measured spectrum reveals that the received signal has a peak power of 58.8 dB, which is in good agreement with the expected value. Also, assuming a 1-GHz detection bandwidth, a minimum SNR of 3 dB, and a noise figure of 3 dB for the LNA, the sensitivity of the UL receiver can be expressed as in (4):

$$UL_{sensitivity} = -174 \text{ dBm} + SNR_{min} + NF + 10 \times \log(BW) = -78 \text{ dBm} \quad (4)$$

Figure 22:
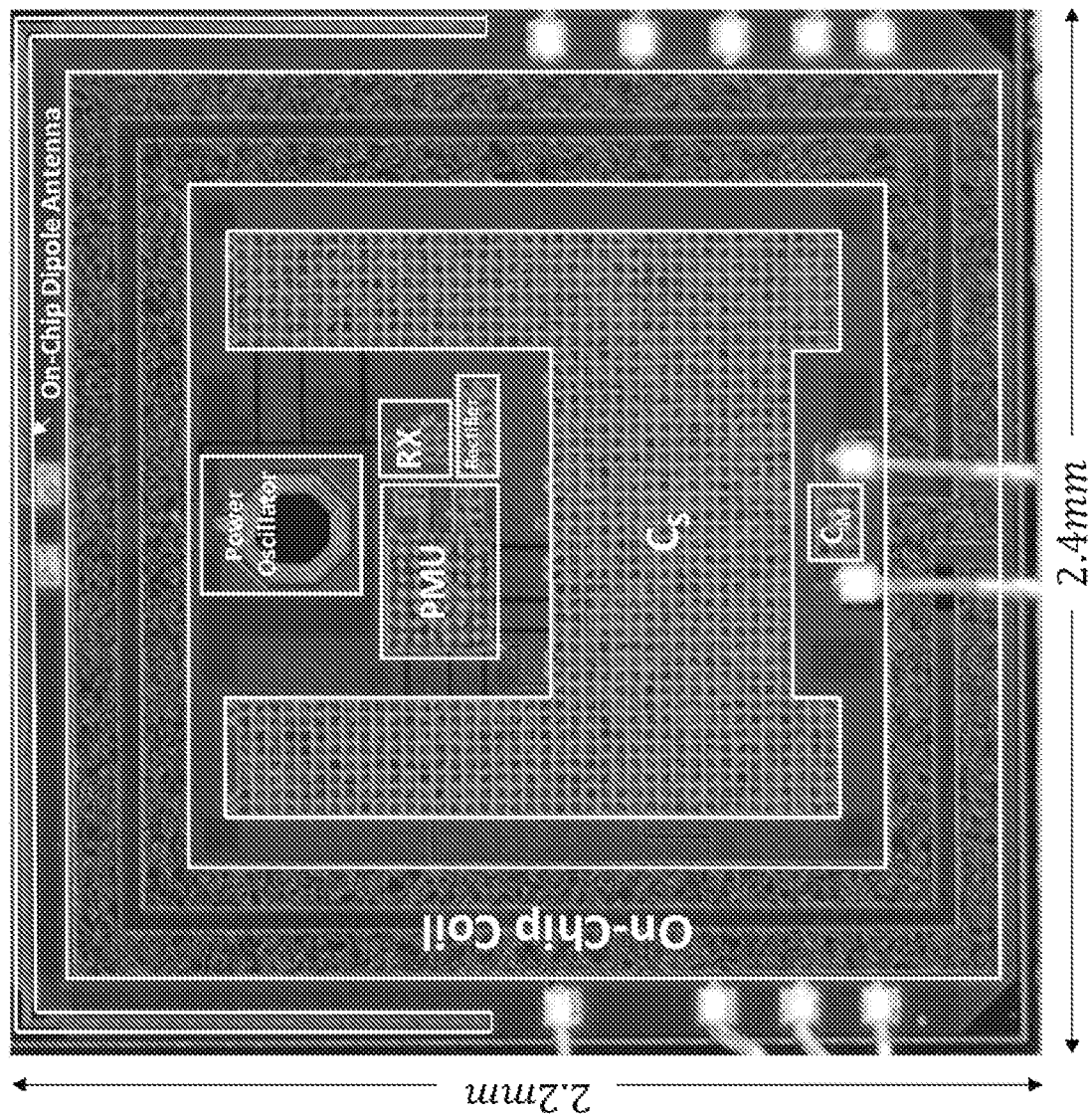
FIG. 22 illustrates an annotated micrograph of a wirelessly powered transceiver in accordance with several embodiments of the invention.

The performance of a wirelessly powered FDD radios in accordance with several embodiments of the invention is summarized in FIG. 21 and compared with state-of-the-art area-constrained TRXs for medical applications. The radio achieves an UL energy efficiency of 4.7 pJ/b and a DL energy efficiency of 1 pJ/b, respectively. Compared with TRXs that utilize any type of antenna for communication, this work shows a ×2.3 improvement in UL and a ×50 improvement in DL energy efficiency values. Also, this design is the first active radio that is fully integrated and does not require any post-processing or off-chip components, which has resulted in a substantial volume reduction. The annotated micrograph of the chip is shown in FIG. 22 and it is evident that the majority of the area is occupied by the antennas and the storage capacitor. The thickness of the die is about 300 μm and the total volume of the design is 2.4×2.2×0.3 mm³. In further embodiments, the volume could be further reduced by grinding the substrate of the chip that improves the performance of antennas as well.

pH Sensor Implementations

In further embodiments of the invention, a wirelessly powered integrated circuit can include an electrochemical sensor and be configured to transmit a signal indicative of an output level from the electrochemical sensor. For example, the electrochemical sensor may be a pH sensor and the output level a measure of pH. As mentioned further above, just as transistor sizes has become smaller, there are now many electrochemical sensors that can be produced in the micrometer scale. Ion-sensitive field effect transistors (IS-FET) and microelectrodes are such examples of micrometer-scaled electrochemical sensors. Designing a circuit that is sensitive enough to be able to read the signals generated from these electrochemical sensors can reduce the form factor, fabrication cost, and time of the overall electrochemical sensing system.

A general pH sensing architecture can include a biasing circuit for the pH electrode to account for both positive and negative swings of the voltage, and a high impedance amplifier to measure the output voltage of the electrode. This scheme can be applied in certain embodiments of the invention. To bias the pH electrode using a unity gain amplifier, the input resistor network can be replaced by diode connected transistors connected in series to achieve high resistance using smaller components, to reduce overall power consumption. For the high input impedance amplifier, an instrumentation amplifier can be used, as it has a high input impedance, and a high common-mode rejection ratio (CMRR). Also, as the pH electrode has a very weak signal that make it more susceptible to noise, using an instrumentation amplifier which has a differential input can help filter out the noise that is coupled into the signal.

Another issue in previous designs is the ambiguity of the transmitter center frequency which can vary from one chip to another. Not only does this make it very difficult to know the exact pH value that was measured by the chip, but it can also interfere with the power link communication if the difference in frequency is not large enough. Therefore, it is desirable to explore digital transmitters which can provide a very accurate center frequency.

Wirelessly Powered pH Sensor Architecture

Figure 23:
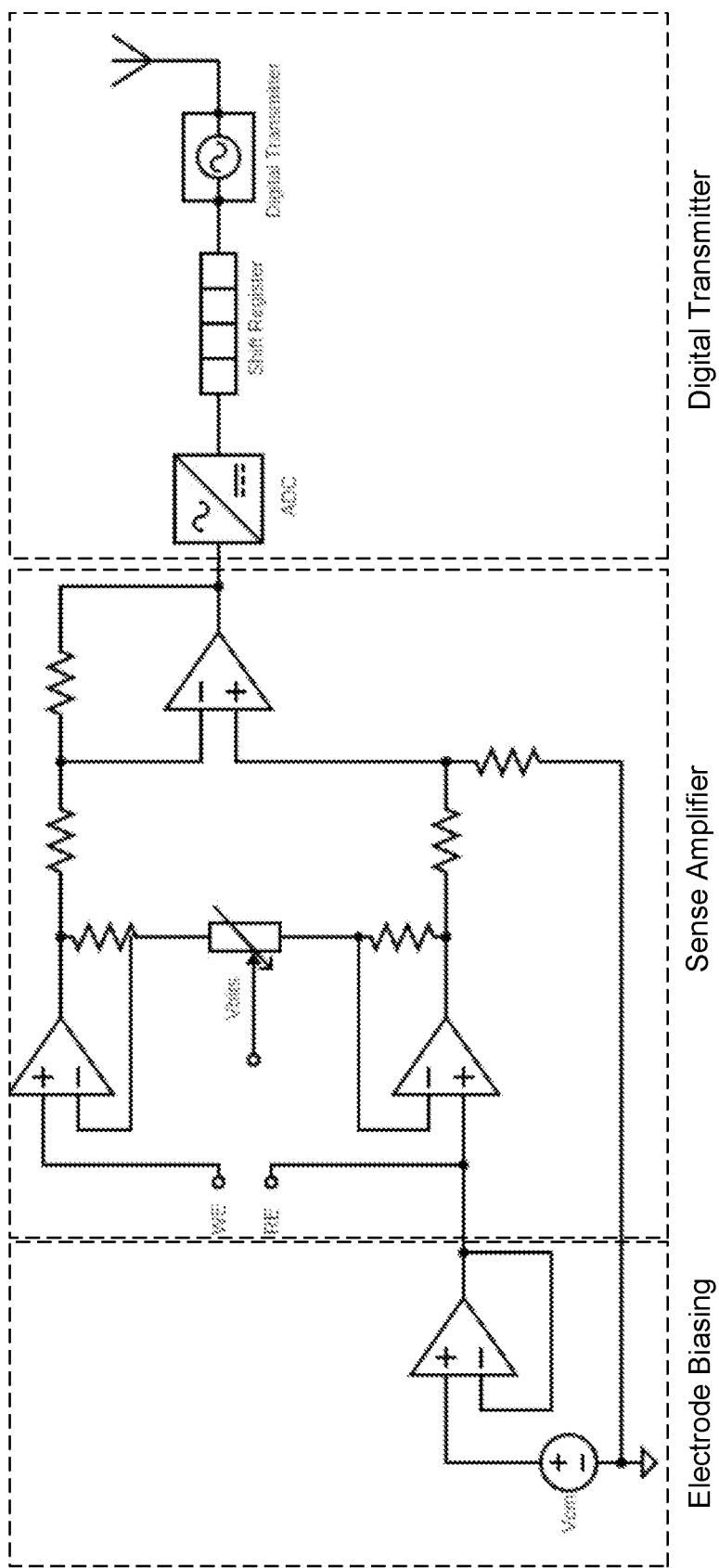
FIG. 23 illustrates a system architecture for a wirelessly powered pH sensor circuit in accordance with several embodiments of the invention.

A system architecture for a wirelessly powered pH sensor circuit in accordance with several embodiments of the invention is shown in the block diagram in FIG. 23. Additional embodiments of the invention can include blocks for a finite state machine (FSM), power receiver rectifier, and/or a clock recovery as discussed with respect to other embodiments further above. In the transmitter block, an analog-to-digital converter (ADC) can be used to read the measured voltage from the sensing circuit, which is digitized (e.g., into 10 bits of digital code), and serially outputted from a shift register to be transmitter through a digital transmitter. By using this architecture, it is possible to recover the exact measured voltage value of the pH electrode when the digital code is converted back to an analog signal at a base station.

Figure 24:
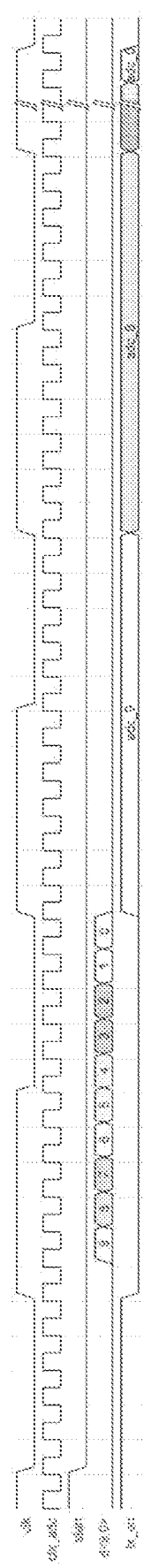
FIG. 24 illustrates a timing diagram for a wirelessly powered pH sensor circuit in accordance with several embodiments of the invention.

With addition of digital blocks in the architecture, an FSM can ensure that the timing of ADC is in sync with the rest of the circuit. Therefore, a reliable clock source and an FSM can be implemented, as well as a voltage rectifier to power the entire circuit. Certain embodiments utilize a SAR-ADC which has a very low power consumption and requires 11 cycles to set up the digital bits once a voltage is measured. An 11 kHz clock signal may be used to drive the ADC and a 1 kHz clock to operate the remainder of the circuit. Methods to generates this clock signal are described further below. A timing diagram of the overall system is in FIG. 24. First, a start signal initializes the circuit turning the transmitter on and off over 2 clock cycles. On the next rising edge of the clock, a voltage value is read which is digitized into 10-bit digital code throughout 11 clock cycles of the ADC clock. At the next rising edge of the clock, the digital bits are loaded onto a shift register simultaneously, and serially outputted over the next 10 clock cycles. In total, 1 pH measurement takes up 12 clock cycles (12 ms) to transmit the measured voltage value to a base station. A 40.68 MHz signal can be used for the power link and 13.56 MHz can be used for the transmitter to avoid interference between the uplink and downlink communication. Although specific characteristics, such as frequencies and bit counts, are discussed above, one skilled in the art will recognize that any of a variety of values may be utilized in accordance with embodiments of the invention as may be suitable for a particular application. Next will discuss the circuit design of major blocks and its simulated results.

pH Sensing Circuit

In certain embodiments, a pH sensing circuit should report back the exact voltage value that was measured by the pH electrode, so the transistor (Rx) is left open and resistors R1 and R2 are equal to make the gain of circuit to be unity. In further embodiments of the invention for other applications, different resistor values can be inserted into the Rx node to vary the gain of the amplifier from 1 through 5.

A single instrumentation amplifier can include 3 operational amplifiers, so it is important that each of these amplifiers draw very little quiescent current. It is also important to have a high gain for each operational amplifier to ensure that the instrumentation amplifier has a near ideal input and voltage characteristics. In some embodiments of the invention, the operational amplifier was designed to have a high gain, have a high PSRR, and to operate in the subthreshold region. Generally, transistors provide the highest transconductance when they are biased in the subthreshold region, therefore, the power consumption of the amplifiers can be reduced in exchange for using wider transistors which occupy more area on the chip.

Figure 25:
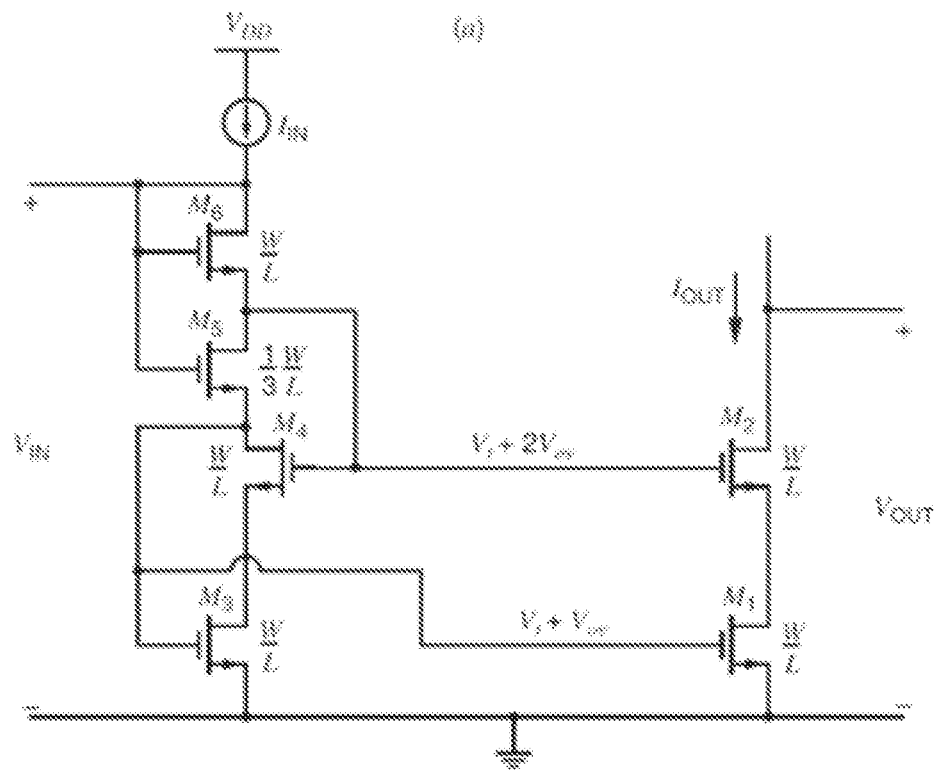
FIG. 25 illustrates a sooch current mirror in accordance with several embodiments of the invention.

A sooch current mirror can be used to force the differential amplifiers to operate in the subthreshold region, as it provides a very stable output voltage due to the cascode transistor M5 such as the configuration shown in FIG. 25. A 2-stage PMOS differential pair may be utilized as it has a higher PSRR. Simulated results showed that the operational amplifier has an open loop gain of over 60 dB, PSRR>56.4 dB, CMRR>80.1 dB and an average power consumption of ~3.5 uW at 1.1V supply voltage.

Digital Transmitter for pH Sensor

A digital transmitter circuit in certain embodiments of the invention operates at 13.56 MHz in the lower ISM band with a 3.3V supply to generate higher power at the transmitter antenna. A delay line is included to produce a pulse that turns on the transmitter for approximately 1 us in order to reduce the power consumption of the transmitter circuit.

In several embodiments of the invention, the waveform of the transmit signal is locked to the phase and/or formation of the receive signal. Various embodiments of the invention may utilize different data transmission techniques.

Figure 26:
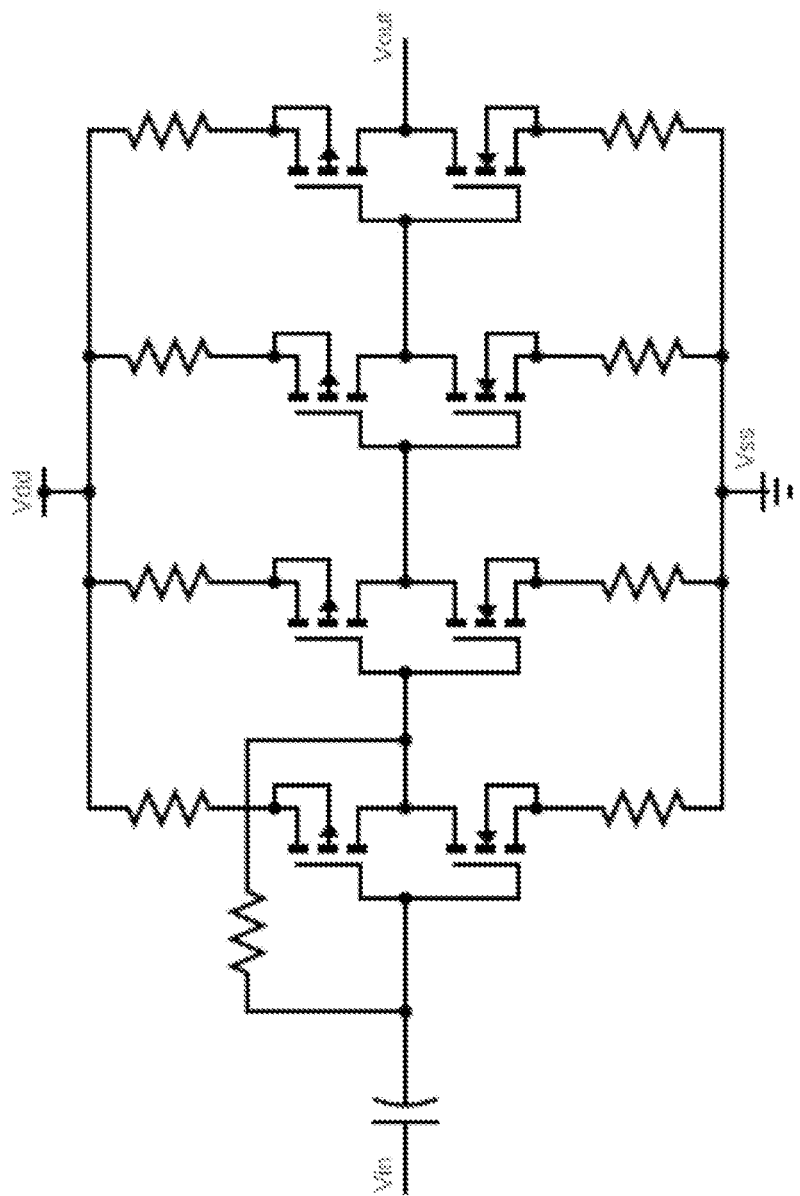
FIG. 26 illustrates a current starved inverter chain for a wirelessly powered pH sensor circuit in accordance with several embodiments of the invention.
Figure 27:
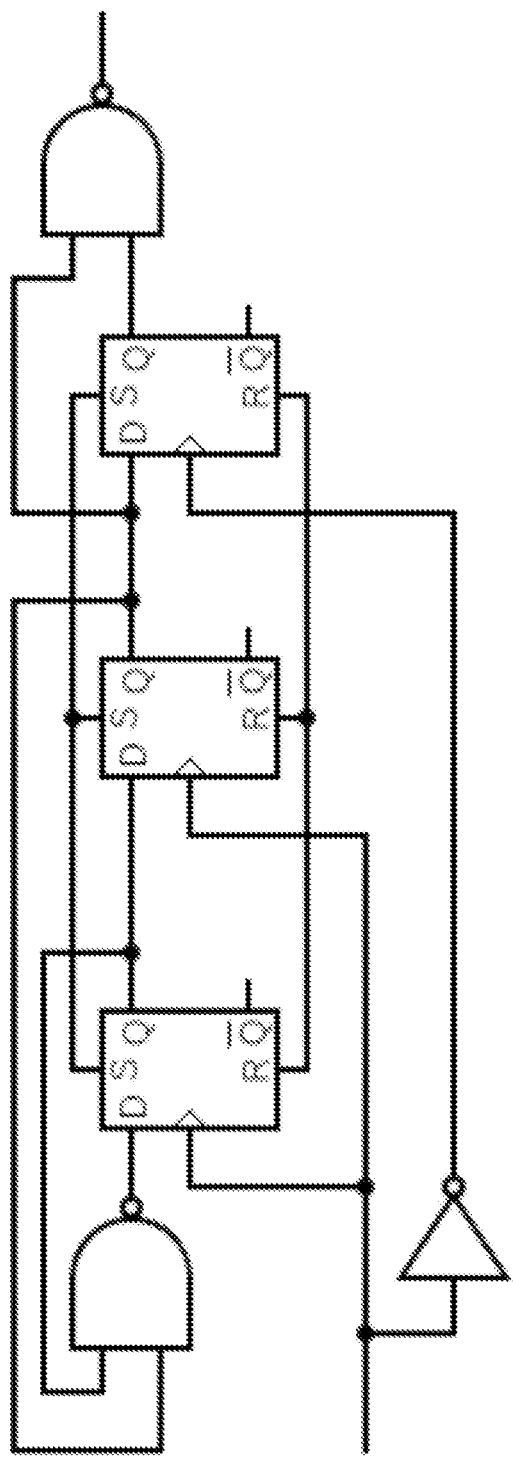
FIG. 27 illustrates a divide-by-three circuit for a wirelessly powered pH sensor circuit in accordance with several embodiments of the invention.

To operate the transmitter at an exact frequency of 13.56 MHZ, the circuit can utilize a 40.68 MHz power link signal generated from a base station. A current starved inverter chain, shown in FIG. 26, may be utilized to amplify the power link signal with minimum power consumption. Then a divide-by-three circuit, such as one illustrated in FIG. 27 with a 50% duty cycle using low power D-FF, may be utilized to generate a 13.56 MHz baseband signal to drive the transmitter circuit. The transmitter is able to transmit information at an exact center frequency without having to interfere with the power link signal. The transmitter was simulated with a loop antenna model at resonance frequency, and a Q-factor of 10.

Power Harvester for pH Sensor

A pH sensor circuit in accordance with embodiments of the invention may utilize a power harvester system such as those described further above, although a different frequency may be appropriate. Some embodiments utilize a 40.68 MHz power link signal. Similar to the power harvester systems described above a four-stage cross coupled rectifier may be utilized to harvest power for a pH sensor circuit.

Voltage dependence of the cascaded cross coupled rectifier can be described by equation:

$$V_{OUT}=2NV_a-N(V_{thn}+V_{thp})$$

Output voltage of the rectifier increases with each stage, and decreases with the threshold voltage of nmos and pmos transistors. Four stages of the cross coupled rectifier can be used to achieve the desired voltage of 3.3V. Higher threshold voltages degrade the output voltage of the rectifier, therefore a native nmos device was used for the first stage. Although higher output voltage translates to higher power conversion efficiency, there is a tradeoff between the cascaded number of stages and the leakage that results from the transistors in each stage. Minimum sized lengths can be used for the devices, and the width were varied to achieve the highest output voltage. A storage capacitor is tied at the output to store the harvested energy. Several embodiments of the invention utilize both MIM capacitors and MOS capacitor to achieve a total storage capacitance of 3 nF.

A pH sensor circuit in accordance with some embodiments of the invention can have an average power consumption of ~35 uW. Furthermore, the transmitter can consume 7.8 nJ/bit at a bit rate of 1 kHz. Therefore, as long as the energy harvester is able to generate an average power of 35 uW, the entire circuit will be able to operate continuously. A pH sensor circuit in accordance with several embodiments can measure a pH value every second using an MEA microprobe connected to a high impedance amplifier. The pH sensor circuit can perform a successive translation of the measured voltage value to a 10-bit digital code using an ADC, which is then transmitted using a transmitter operating with an on-off keying (OOK) scheme.

Although the description above contains many specificities, these should not be construed as limiting the scope of the invention but as merely providing illustrations of some of the presently preferred embodiments of the invention. Various other embodiments are possible within its scope. Accordingly, the scope of the invention should be determined not by the embodiments illustrated, but by the appended claims and their equivalents.

What is claimed is:

1. A small form-factor, wirelessly powered transceiver on a chip, the transceiver comprising:
    a receive antenna on the chip and comprising a loop antenna configured to receive a receive signal;
    a transmit antenna on the chip and at least partially surrounding the receive antenna and configured to transmit a transmit signal; and
    a power harvesting system comprising:
        a rectifier circuit configured to convert radio frequency energy from the receive signal into DC (direct current) voltage; and
        a power management unit (PMU);
    a receiver circuitry block configured to provide energy from the receive signal to the power harvesting system; and a transmitter circuitry block comprising a data modulator circuit, the data modulator circuit configured to generate the transmit signal using DC voltage received from the power management unit;

wherein the PMU is configured to set an operating mode and biasing condition of the receiver and transmitter circuitry blocks and to provide DC voltage from the receiver circuitry block to the transmitter circuitry block to maintain a minimum voltage.

2. The wirelessly powered transceiver of claim 1, wherein the rectifier circuit comprises four full-wave rectifiers.

3. The wirelessly powered transceiver of claim 1, wherein the rectifier circuit comprises an on-chip coil (OCC).

4. The wirelessly powered transceiver of claim 1, wherein the receive antenna further comprises a capacitor.

5. A small form-factor, wirelessly powered transceiver comprising:
a receive antenna configured to receive a receive signal;
a transmit antenna configured to transmit a transmit signal; and
a power harvesting system comprising:
a rectifier circuit configured to convert radio frequency energy from the receive signal into DC (direct current) voltage;
a power management unit (PMU);
a receiver circuitry block configured to provide energy from the receive signal to the power harvesting system; and
a transmitter circuitry block comprising a data modulator circuit, the data modulator circuit configured to generate the transmit signal using DC voltage received from the power management unit;
wherein the receiver circuitry block further comprises a tunable capacitor configured to change the resonance frequency of the receive antenna to reduce interference with the transmit signal;
wherein the PMU is configured to set an operating mode and biasing condition of the receiver and transmitter circuitry blocks and to provide DC voltage from the receiver circuitry block to the transmitter circuitry block to maintain a minimum voltage.

6. The wirelessly powered transceiver of claim 1, where the transmitter circuitry block comprises a power oscillator.

7. The wirelessly powered transceiver of claim 6, wherein the receiver circuitry block is configured to extract a clock signal from the receive signal and the transmitter circuitry block is configured to synchronize the power oscillator to the clock signal.

8. The wirelessly powered transceiver of claim 1, where the transmitter circuitry block comprises an LC oscillator and power amplifier.

9. The wirelessly powered transceiver of claim 1, further comprising a bioelectrical signal sensor configured to generate a bioelectrical signal to the data modulator circuit.

10. The wireless powered transceiver of claim 9, wherein the bioelectrical signal sensor is a neural LFP (local field potential) sensor.

11. The wirelessly powered transceiver of claim 1, wherein the power management unit includes a low dropout voltage regulator (LDO) configured to change its bias current based upon a sleep and an active state of the transmitter circuitry block.

12. A small form-factor, wirelessly powered transceiver comprising:
a receive antenna configured to receive a receive signal;
a transmit antenna configured to transmit a transmit signal; and
a power harvesting system comprising:
a rectifier circuit configured to convert radio frequency energy from the receive signal into DC (direct current) voltage;
a power management unit (PMU);
a receiver circuitry block configured to provide energy from the receive signal to the power harvesting system; and
a transmitter circuitry block comprising a data modulator circuit, the data modulator circuit configured to generate the transmit signal using DC voltage received from the power management unit;
wherein the receiver circuitry block comprises a data demodulator configured to extract a receive message from the receive signal;
wherein the PMU is configured to set an operating mode and biasing condition of the receiver and transmitter circuitry blocks and to provide DC voltage from the receiver circuitry block to the transmitter circuitry block to maintain a minimum voltage.

13. The wirelessly powered transceiver of claim 1, wherein the receiver circuitry block and transmitter circuitry block are configured to operate at different frequencies.

14. The wirelessly powered transceiver of claim 1, wherein the receiver circuitry block and transmitter circuitry block utilize amplitude-based modulation schemes in the receive signal and transmit signal.

15. The wirelessly powered transceiver of claim 14, wherein the receiver circuitry block utilizes amplitude-shift-keying (ASK) modulation for receiving data in the receive signal and the transmitter circuitry block utilizes frequency divisional duplexing (FDD) for transmitting data in the transmit signal.

16. The wirelessly powered transceiver of claim 1, where the PMU is configured to control the transmitter circuitry block to operate on a duty cycle based upon a current amount of energy stored in a storage capacitor, by deactivating the transmitter circuitry block when voltage across the storage capacitor falls below a lower threshold voltage and activating the transmitter circuitry block when voltage across the storage capacitor exceeds a higher threshold voltage.

17. The wirelessly powered transceiver of claim 1, wherein the transmit antenna is a dipole antenna.

18. The wirelessly powered transceiver of claim 1, wherein the transmit antenna dimensions and operating frequency are optimized to minimize interference from operation of the receive antenna.

19. The wirelessly powered transceiver of claim 1, further comprising an electrochemical sensor configured to generate an electrochemical signal to the data modulator circuit.

20. The wirelessly powered transceiver of claim 19, wherein the electrochemical sensor is a pH sensor configured to provide an electrochemical signal indicative of pH of a solution.

21. The wirelessly powered transceiver of claim 1, wherein the transmit signal can be received as multiple reads and localization of the transceiver is determined from the multiple reads.

22. The wirelessly powered transceiver of claim 21, wherein the localization accuracy is improved by moving the location of the transceiver and repeating the measurement.

23. The wirelessly powered transceiver of claim 22, wherein the localization accuracy is improved by utilizing the phase and amplitude of the read signal as a function of the location of the transceiver.

* * * * *